US005916871A

United States Patent [19]
Johnson

[11] Patent Number: 5,916,871
[45] Date of Patent: Jun. 29, 1999

[54] INHIBITORY FACTOR

[75] Inventor: Terry C. Johnson, Manhattan, Kans.

[73] Assignee: Kansas State University Research Foundation, Manhattan, Kans.

[21] Appl. No.: 08/411,396

[22] Filed: Mar. 28, 1995

Related U.S. Application Data

[63] Continuation of application No. 08/111,261, Jun. 21, 1993, abandoned, which is a continuation-in-part of application No. PCT/US93/03953, Apr. 27, 1993, which is a continuation-in-part of application No. 07/874,128, Apr. 27, 1992, abandoned.

[51] Int. Cl.⁶ .............................................. C07K 14/475
[52] U.S. Cl. ................................. 514/8; 514/2; 514/12; 530/350; 530/351; 530/395
[58] Field of Search ................................. 530/324, 350, 530/351, 399, 402, 395; 435/69.1, 69.4, 69.5; 514/2, 12, 8

[56] References Cited

U.S. PATENT DOCUMENTS

| | | | |
|---|---|---|---|
| 4,708,948 | 11/1987 | Iwata et al. | 514/2 |
| 5,136,021 | 8/1992 | Dembinski et al. | 530/350 |
| 5,187,077 | 2/1993 | Gearing et al. | 435/69.1 |
| 5,214,031 | 5/1993 | Uchida | 514/12 |
| 5,231,012 | 7/1993 | Mosmann et al. | 435/69.5 |
| 5,268,455 | 12/1993 | Cianciolo | 530/404 |
| 5,304,541 | 4/1994 | Purchio et al. | 514/12 |

FOREIGN PATENT DOCUMENTS

| | | |
|---|---|---|
| 0 315 289 | 5/1989 | European Pat. Off. . |
| 0 322 084 | 6/1989 | European Pat. Off. . |
| 0 458 673 | 11/1991 | European Pat. Off. . |
| WO 92/07938 | 5/1992 | WIPO . |

OTHER PUBLICATIONS

Page, D. et al., *J. Immunology*, 140(11): 3717–26, 1988.
Smeland, E.B. et al., *Exp. Cell Res.*, 171: 213–222, 1987.
Elgjo, K et al., *J. Invest. Dermatol.*, 87(5): 555–8,1986.
Kim, K.–M. et al., *J. Immunology*, 148(6): 1797–1803, 1992.
Kinders, et al, Biochem. Biophys. Res. Commun., v. 124, No. 1, 1984, pp. 133–140, "A Monoclonal Antibody to a Unique Cell Surface Growth Regulatory Glycopeptide".
Sharifi et al, "Use of a Urea and Guanidine–HC1–Propanol Solvent System to Purify A Growth Inhibitory Glycopeptide by High–Performance Liquid Chromatography", Journal of Chromatography, 324 (1985) 173–180.
Bascom et al, "Receptor Occupancy by a Bovine Sialoglycopeptide Inhibitor Correlates with Inhibition of Protein Synthesis", Journal of Cellular Physiology, 128:202–208 (1986).
Sharifi et al, "Purification and Characterization of a Bovine Cerebral Cortex Cell Surface Sialoglycopeptide that Inhibits Cell Proliferation and Metabolism", Journal of Neurochemistry, pp. 461–469 (1986).
Sharifi et al, "Relationship Between Protease Activity and a Sialoglycopeptide Inhibitor Isolated from Bovine Brain", Journal of Cellular Biochemistry 31:41–57 (1986).

Sharifi et al, "Cell Surface Interaction is Sufficient for the Biological Activity of a Bovine Sialoglycopeptide Inhibitor", Biochemical and Biophysical Research Communications, vol. 134, No. 3, 1986, pp. 1350–1357.
Sharifi et al, "The Effects of a Calcium and a Sodium Ionophore on Protein Synthesis Inhibition by a Bovine Cell Surface Sialoglycopeptide", vol. 136, No. 3, 1986, Biochemical and Biophysical Research Communications, pp. 976–982.
Sobieski et al, "Cell Agglutination by a Novel Cell Surface Sialoglycopeptide Inhibitor and the Relationship Between its Protease and Biological Activities", Life Sciences, vol. 38, pp. 1883–1888.
Bascom et al, "Inhibition of Epidermal Growth Factor–Stimulated DNA Synthesis by a Bovine Sialoglycopeptide Inhibitor Occurs at an Intracellular Level", Journal of Cellular Biochemistry 34:283–291 (1987).
Chou et al, "A Unique Sialoglycopeptide Growth Regulator that Inhibits Mitogenic Activity of a Phorbol Ester Tumor Promoter", Cancer Letters, 35 (1987), pp. 119–128.
Sharifi et al, "Affinity Labeling of the Sialoglycopeptide Antimitogen Receptor", The Journal of Biological Chemistry, vol. 262, No. 32, Issue of Nov. 15, pp. 15752–15755, 1987.
Fattaey et al, "Inhibition of DNA Synthesis and Cell Division by a Cell Surface Sialoglycopeptide", Journal of Cellular Physiology, 139:269–274 (1989).
Johnson et al, "Abrogation of the Mitogenic Activity of Bombesin by a Cell Surface Sialoglycopeptide Growth Inhibitor", Biochemical and Biophysical Research Communications, vol. 161, No. 2, 1989, pp. 468–474.
Edson et al, "Cell Cycle Arrest and Cellular Differentiation Mediated by a Cell Surface Sialoglycopeptide", Life Sciences, vol. 48, pp. 1813–1820 (1991).
Fattaey et al, "Modulation of Growth–Related Gene Expression and Cell Cycle Synthronization by a Sialoglycopeptide Inhibitor", Experimental Cell Research 194, 62–68 (1991).
Toole–Simms et al, "Effects of a Sialoglycopeptide on Early Events Associated with Signal Transduction", Journal of Cellular Physiology, 147:292–297 (1991).
Lakshmanarao et al, "Identification of a Cell Surface Component of Swiss 3T3 Cells Associated with an Inhibition of Cell Division", Experimental Cell Research 195, 412–415 (1991).
Johnson et al, "The Role of A Cell Surface Inhibitor in Early Signal Transduction Associated with the Regulation of Cell Division and Differentiation", Transactions of the Kansas Academy of Science 95(1–2):11–15 (1992).
Enebo et al, "The Use of the Tyrosine Phosphatase Antagonist Orthovanadate in the Study of a Cell Proliferation Inhibitor", Transactions of the Kansas Academy of Science, 96(1–2):40–45 (1993).
Fattaey et al, "The Identification of a Naturally Occurring Cell Surface Growth Inhibitor Related to a Previously Described Bovine Sialoglycopeptide", Journal of Cellular Biochemistry 52:69–787 (1993).

Primary Examiner—Marianne P. Allen
Attorney, Agent, or Firm—Nixon & Vanderhye P.C.

[57] ABSTRACT

Novel inhibitory factors, oligonucleotides encoding the same, and methods of production are disclosed. Pharmaceutical compositions and methods of treating disorders are also disclosed.

16 Claims, 13 Drawing Sheets

Fig. 1

|  | Isotonic Buffer | 3M NaCl | 3M Urea |
|---|---|---|---|
| Released | A) | C) | E) |
| Bound | B) | D) | F) |

A: 100 μg of Plasma membrane

B: 50 μg of NaCl released

C: 10 μg of IEF (ROTOFER Purified)

D: 5 μg of LPA purified.

Incubation Time (h)

Incubation Time (h)

Incubation Time (h)

Inhibition of Hybridoma Cell Proliferation

INHIBITORY FACTOR

This is a continuation of application Ser. No. 08/111,261, filed Jun. 21, 1993, now abandoned, which in turn is a continuation-in-part of PCT/US93/03953 filed Apr. 27, 1993, which is a continuation-in-part of U.S. Ser. No. 07/874,128 filed Apr. 27, 1992, now abandoned.

FIELD OF THE INVENTION

The present invention relates to factors that mediate mammalian cell cycle arrest and maintain mammalian cells in a viable state, the use of such factors, and to nucleic acid sequences encoding such factors. In particular the invention relates to these factors, to fragments and polypeptide analogs thereof and to DNA sequences encoding the same.

BACKGROUND OF THE INVENTION

Both growth factors (stimulators of cell cycling) and growth inhibitory factors (inhibitory factors of cell cycling) play an important role in cell-cell interactions and cell division. Despite the practical importance of growth inhibitory factors, very few have been isolated and purified and, in most cases, there is little evidence that the biologically active inhibitory factors previously isolated are residents of the cell surface or act by binding cell surface receptors. The existence of cell surface inhibitory factors would be consistent with the models of regulation of cell division as a result of cell-cell contact.

Compared to the numerous growth factors that have been described, very few inhibitory factors of cell proliferation have been isolated and characterized. The major inhibitory factors described include: 1) the 25 kDa homodimer transforming growth factor-β (TGF-β) that has mitogenic activity with a variety of fibroblasts and yet expresses a potent inhibitory activity with normal human epithelial prokeratinocytes cultured in serum-free medium (Roberts et al., Proc. Natl. Acad. Sci. U.S.A., 82: 119–123, 1985; Coffey et al., Cancer Res. 48: 1596–1602, 1988) and the structurally-related protein isolated from African green monkey cells (BCS-1) conditioned medium (Tucker et al., Science 226: 705–707, 1984); 2) a 12–14 kDa protein isolated from mammary tissue (Bohmer et al., Exp. Cell Res. 150: 466–476, 1984; Muller et al., J. Cell. Physiol. 138: 415–423, 1989) that has been identified in cell nuclei and shown to be structurally related to a fibroblast growth inhibitory factor isolated from mouse 3T3 cell medium (Voss et al., Exp. Cell Res. 138: 397–407, 1982; Bohmer et al, J. Cell. Biochem. 38: 199–204, 1988); 3) a 17 kDa acidic protein, originally described as a glial maturation factor β, that has been shown to have antiproliferative activity (Lim, Proc. Natl. Acad. Sci. U.S.A. 86: 3901–3905, 1989; Lim et al., Cell Regulat. 1: 741–746, 1990); 4) an oligosaccharide from human diploid fibroblasts (Wieser et al., J. Cell Biol. 111: 2681–2692, 1990); 5) a tissue-specific growth inhibitory factor (mammostatin) isolated from cell culture medium (Ervin et al., Science 244: 1585–1587, 1989); and, 6) two classes of glycopeptide inhibitory factors structurally unrelated to the present invention (Kinders et al., Exp. Cell Res. 136: 31–41, 1981; Charp et al., J. Cell Biol. 97: 311–316, 1983).

Cell proliferation inhibitory factors that are membrane residents and that play a role in cell-cell signaling, most likely have significant hydrophobic domains, or are complexed with hydrophobic integral membrane components. This feature has led to technical difficulties in their isolation, identification, and their presentation to target cells for meaningful biological assays—particularly when detergents (necessary to maintain the elements in aqueous suspension or solution) are toxic solvents to living cells.

A hydrophilic and active fragment of a larger glycoprotein inhibitory factor was released from intact cells that allowed purification by biochemical procedures (Sharifi et al., J. Chromat. 324: 173–180, 1985; Sharifi et al., Neurochem. 46: 461–469, 1986a).

The bovine inhibitory glycopeptide is composed of a single polypeptide chain of a molecular weight of approximately 18,000 that focuses by isoelectric focusing at about 3.0 (Sharifi et al, Neurochem. 46: 461–469, 1986; and Sharifi et al, J. Cell. Biochem. 31: 41–47, 1986). The glycopeptide inhibits cellular protein and DNA synthesis, and arrests cells in the mitotic cycle at what appears to be a single block point near the $G_1/S$ interphase (Fattaey et al., J. Cell. Physiol. 139: 269–274, 1989; and Fattaey et al, Exper. Cell Res. 194: 62–68, 1991). The glycopeptide inhibitory factor requires only a cell surface interaction to mediate its biological inhibitory activity (Sharifi et al., Biochem. Biophys. Res. Comm. 134: 1350–1357, 1986c), and the binding kinetics are consistent with a specific and saturable cell surface receptor (Bascom et al., J. Cell Physiol. 128: 202–208, 1986; Sharifi and Johnson, J. Biol. Chem. 262: 15752–15755, 1987).

Consistent with the hypothesis that cell division is controlled by the interaction of ligands at the cell surface with both positive and negative influences, the glycopeptide has been identified on the surfaces of 3T3 cells (Lakshmanarao et al., Exper. Cell Res. 195: 412–415, 1991), and to be a potent antagonist of the tumor promoter 12-O-tetradecanoylphorbol-13-acetate (TPA) (Chou et al., Cancer Lett. 35: 119–128, 1987), epidermal growth factor (EGF) (Bascom et al., J. Cell. Biochem. 34: 283–291, 1987) and bombesin (Johnson and Sharifi, Biochem. Biophys. Res. Comm. 161: 468–474, 1989).

Although the glycopeptide was isolated from bovine cerebral cortex cells, its inhibitory action is effective on wide range of target cells. Cells sensitive to its proliferative inhibitory action include vertebrate and invertebrate (insect) cells, fibroblast and epithelial-like cells, primary cells and established cell cultures, as well as a wide range of transformed cell lines (Fattaey et al., J. Cell. Physiol. 139: 269–274, 1989; and Fattaey et al, Exper. Cell Res. 194: 62–68, 1991).

With the exception of one cell line, human HL-60 leukemic cells, all cells which were inhibited were reversibly inhibited by the glycopeptide in a nontoxic manner (Edson et al, Life Sci. 48: 1813–1820, 1991). HL-60 cells, however, were arrested in an irreversible fashion although they remained viable for at least 84 h. The glycopeptide mediated a terminal cellular differentiation, even after its removal.

An interesting feature of the glycopeptide is that the biological inhibitory activity clearly is $Ca^{2+}$ dependent, and possibly related to cellular $Ca^{2+}$ fluxes and/or intracellular $Ca^{2+}$ mobilization (Toole-Simms et al., J. Cell. Physiol. 147: 292–297, 1991). The addition of the calcium ionophore A23187, but not the sodium ionophore monensin, before or within minutes of the inhibitory factor, results in the abrogation of the inhibition of protein synthesis (Sharifi et al., Biochem. Biophys. Res. Comm. 136: 976–982, 1986).

Prior to the subject invention, a particularly disturbing feature of the purified glycopeptide was that a protease activity, of unknown specificity, always was measurable in even the most purified preparations (Sharifi et al., J. Cell. Biochem. 31: 41–47, 1986). Whether the protease was an integral activity of the glycopeptide molecule itself, or a trace contaminant in the purified preparations could not be determined. Although the protease activity remained even when the biological inhibitory activity of the glycopeptide was destroyed (Sobieski et al., Life Sci. 38: 1883–1888, 1986), the proteases presence was unavoidable and complicated the preparation of samples for studies of protein sequencing.

OBJECTS OF THE INVENTION

It is an object of the invention to provide a method of purifying naturally occurring inhibitory factor to apparent homogeneity.

It is an object of the invention to provide DNA and RNA sequences encoding inhibitory factor.

It is an object of the invention to provide recombinant polypeptide factors which inhibit cell division.

It is a further object of the invention to provide factors which can be used alone or in combination with other agents in the treatment of neoplastic or proliferative states or states relating to cell proliferation in a variety of species.

It is a further object of the invention to provide factors which can slow growth, development or aging.

SUMMARY OF THE INVENTION

According to the present invention, polypeptide factors, referred to herein as "inhibitory factor" having the ability to inhibit cell division or cell cycling, are provided. Such factors include purified naturally-occurring inhibitory factors. The invention also relates to non-naturally occurring polypeptides having amino acid sequences sufficiently duplicative of that of naturally-occurring inhibitory factor to allow possession of a biological activity of naturally occurring inhibitory factor such as the ability to inhibit cell division.

The present invention also provides isolated nucleic acid sequences for use in securing expression in procaryotic or eucaryotic host cells of polypeptide products having amino acid sequences sufficiently duplicative of that of naturally-occurring inhibitory factors to allow possession of a biological activity of naturally occurring inhibitory factor. Such DNA sequences include:

a) DNA sequences encoding naturally occurring inhibitory factor disclosed in Example VII or their complementary strands;

b) DNA sequences which hybridize to the DNA sequences defined in a) or fragments thereof; and c) DNA sequences which, but for the degeneracy of the genetic code, would hybridize to the DNA sequences defined in a) and b).

The invention also provides modified or substituted nucleic acid sequences (methyl phosphonate, thiolate, etc.) which bind to sequences either encoding inhibitory factor or complementary to those coding for inhibitory factor.

Also provided are vectors containing such DNA sequences, and host cells transformed or transfected with such vectors. Also comprehended by the invention are methods of producing inhibitory factors by recombinant techniques, and methods of treating disorders. Additionally, pharmaceutical compositions including inhibitory factors are provided. Antibodies specifically binding inhibitory factors are also provided.

The invention also relates to a process for the efficient recovery of inhibitory factors from a material containing inhibitory factors.

BRIEF DESCRIPTION OF THE DRAWINGS

FIG. 1 shows an immunoblot analysis of components released from bovine brain cerebral cortex cell membrane. Equal aliquots of plasma membrane were incubated for 30 min. at 4° C. with either isotonic buffer alone (0.154M NaCl; 0.01M potassium phosphate; 1 $\mu g/\mu l$ each of phosphoramidon, pepstatin A, leupeptin and aprotinin; pH 7.2), or with isotonic buffer containing either 3M NaCl or 3M urea. After incubation the membranes were pelleted by centrifugation as described in the Materials and Methods and 100 $\mu l$ of each supernatant fluid where tested for antigenicity as membrane released material (slots A, C and E). The membrane pellets were solubilized in 1% octyl-$\beta$-D-glucopyranoside (2.5 mg protein/ ml) and 100 $\mu l$ were tested for antigenicity as membrane bound material (slots B, D and F).

(RB⁻) and human prostate carcinoma DU145 (RB⁻) cell lines. Carcinoma cells grown in DMEM and 10% fetal calf serum, and either $9\times10^{-8}$M inhibitory factor (○) or an equal volume of PBS (●) was added at the time indicated by the arrows. Data are plotted as the average of duplicate wells.

Figure 8A:
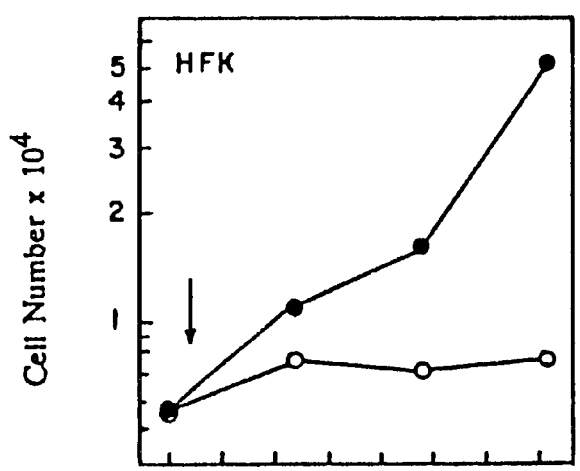
Figure 8B:
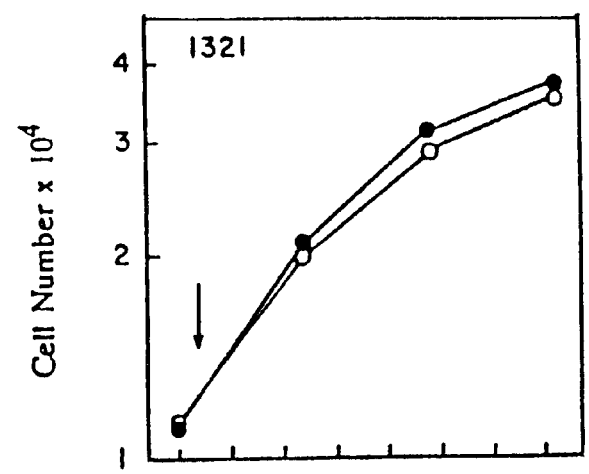
Figure 8C:
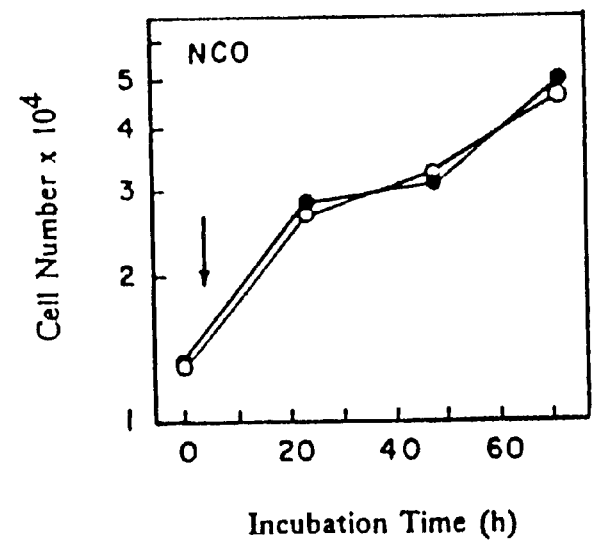

FIG. 8 shows inhibitory factor cell proliferation inhibition assays carried out on the human keratinocyte HFK (normal) and human papillomavirus transformed (1321 and NCO) cell lines. Cells were grown in KGM medium with appropriate growth factors (Clonetics, San Diego, Calif.), and either $9\times10^{-8}$M inhibitory factor (○) or an equal volume of PBS (●) was added at the time indicated by the arrows. Data are plotted as the average of duplicate wells.

Figure 9:
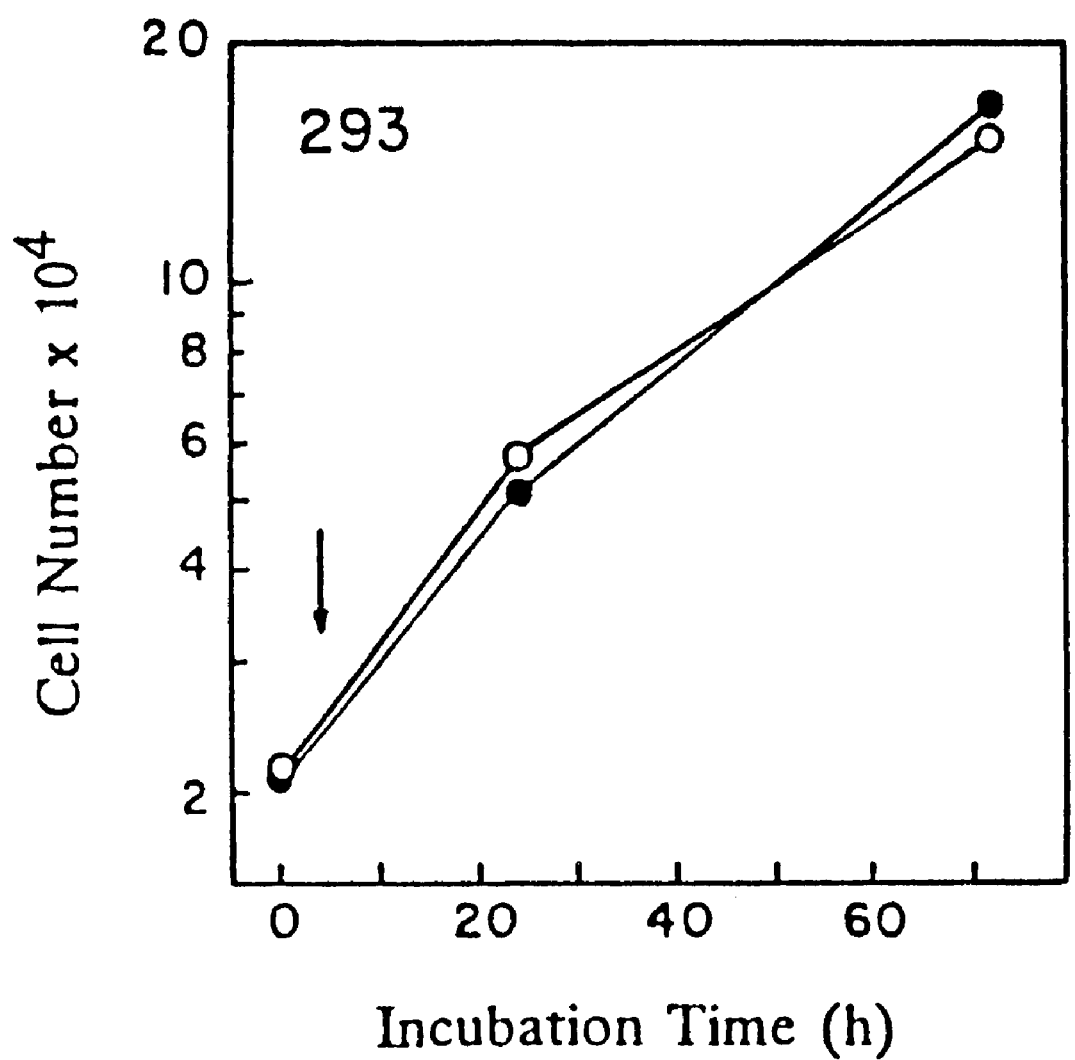

FIG. 9 shows inhibitory factor cell proliferation inhibition assays carried out on the adenovirus transformed human kidney epithelial cell line 293. Cells were grown in DMEM and 10% fetal calf serum, and either $9\times10^{-8}$M inhibitory factor (○) or an equal volume of PBA (●) was added at the time indicated by the arrows. Data are plotted as the average of duplicate wells.

Figure 10A:
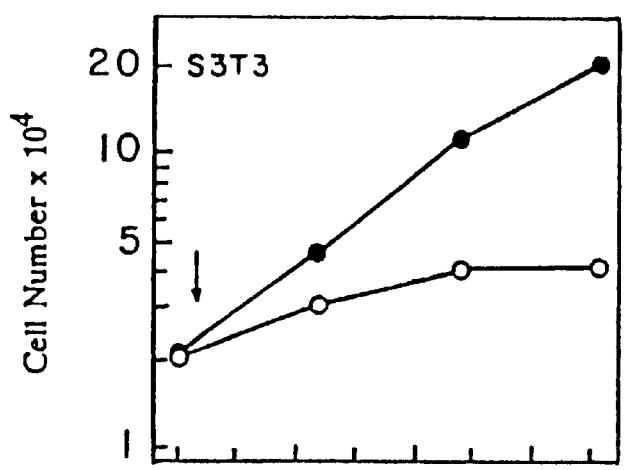
Figure 10B:
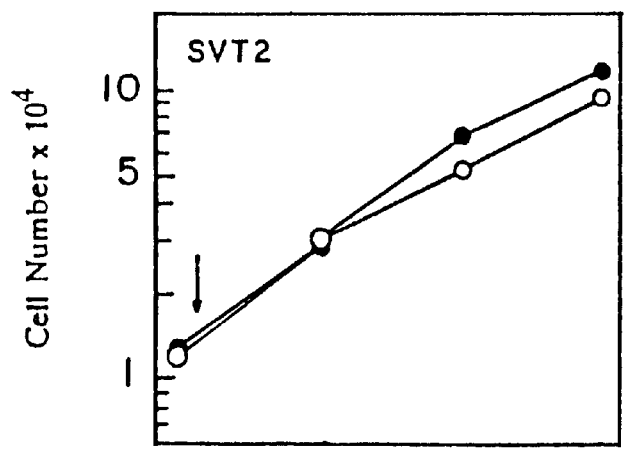
Figure 10C:
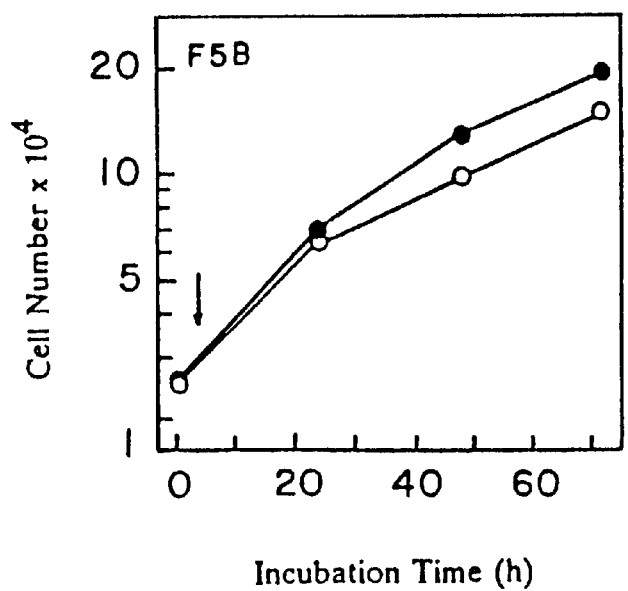

FIG. 10 shows inhibitory factor cell proliferation inhibition assays carried out on the murine fibroblast Swiss 3T3 (normal) and SV40 transformed (SVT-2 and F5B) cell lines. Fibroblasts were grown in DMEM and 10% calf serum, and either $9\times10^{-8}$M inhibitory factor (○) or an equal volume of PBA (●) were added at the time indicated by the arrows. Data are plotted as the average of duplicate wells.

Figure 11:
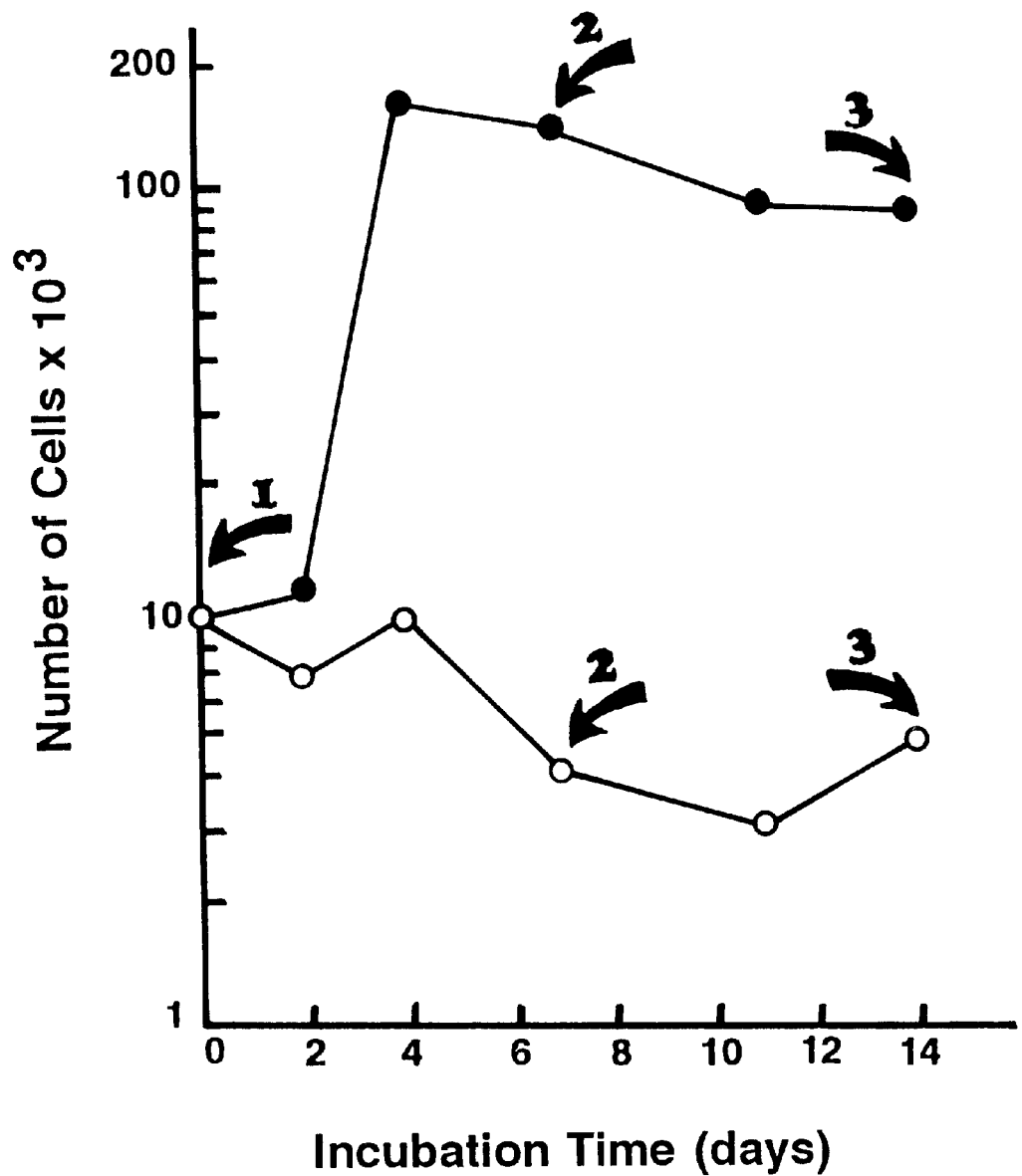

FIG. 11 shows inhibition of hybridoma cell proliferation

Figure 12A:
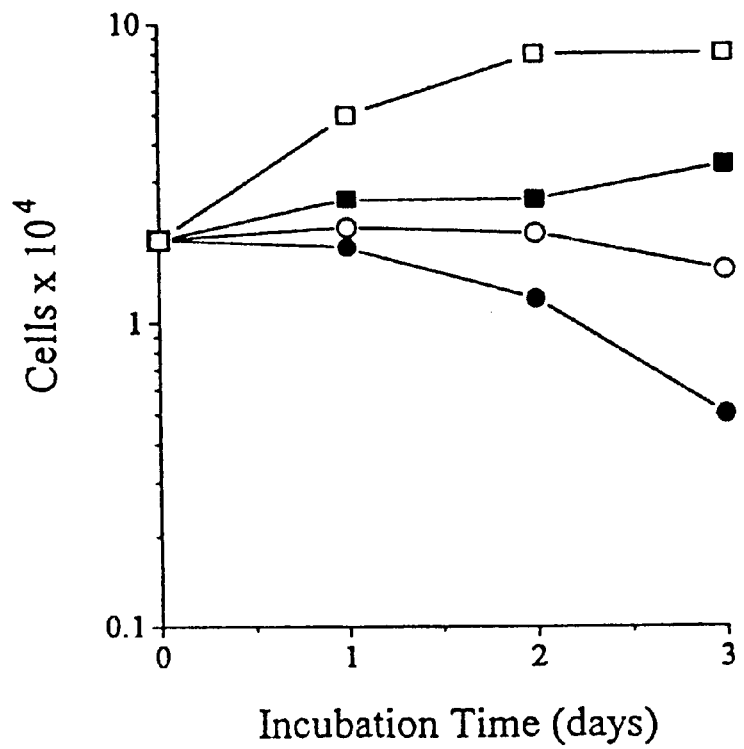
Figure 12B:
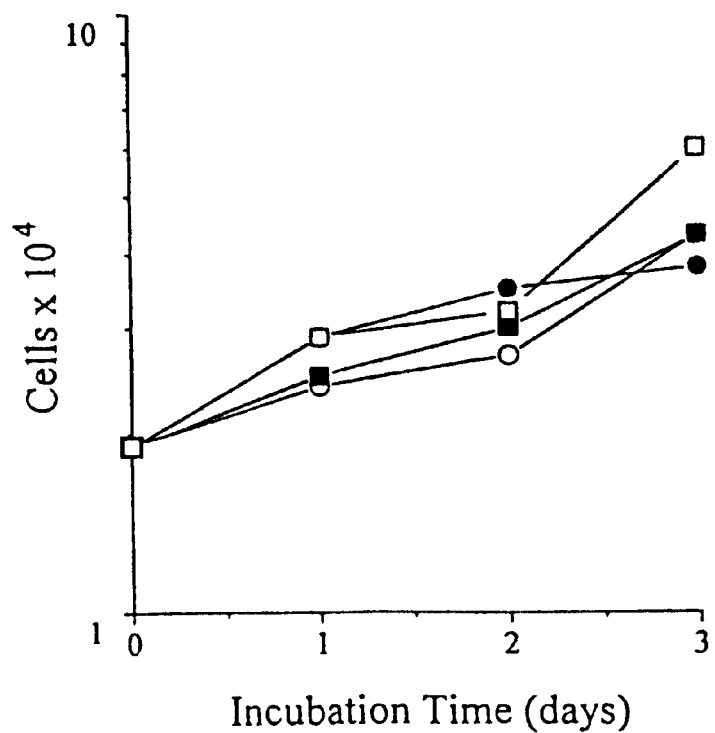

FIG. 12A–B shows effect of the extracellular calcium concentration on inhibitory factor-induced growth inhibition in 308 transformed mouse keratinocytes. Cells were treated at time 0 with PBS (open squares), $5\times10^{-10}$M inhibitory factor (filled boxes), $5\times10^{-9}$M inhibitory factor (open circles), or $3\times10^{-8}$M inhibitory factor (filled circles) in Eagle's minimal essential medium containing (A) 0.05 mM $Ca^{2+}$ or (B) 1.4 mM $Ca^{2+}$. Cell proliferation was monitored in 48-well plates at the times indicated.

Figure 13A:
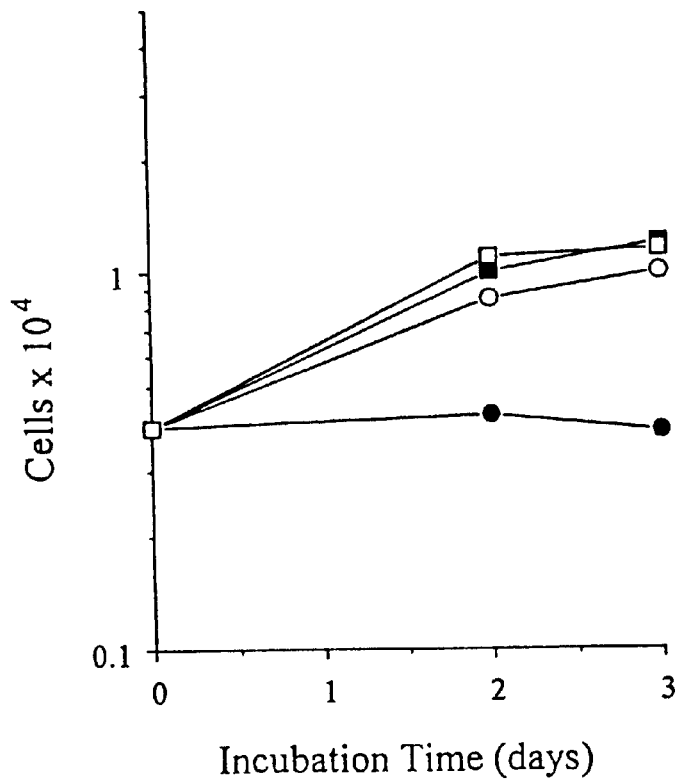
Figure 13B:
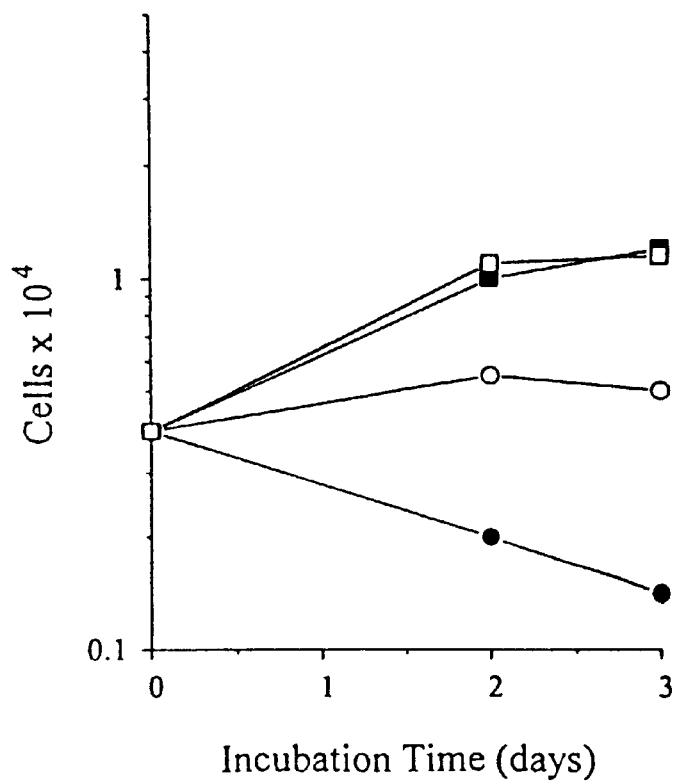

FIG. 13A–B shows effect of the extracellular calcium concentration on inhibitory factor-induced growth inhibition of S3T3 mouse fibroblasts. Cells were treated at time 0 with PBS (open squares), $5\times10^{-10}$M inhibitory factor (filled boxes), $5\times10^{-9}$M inhibitory factor (open circles), or $3\times10^{-8}$M inhibitory factor (filled circles) in Eagle's minimal essential medium containing (A) 1.8 mM $Ca^{2+}$ or (B) 0.18 mM $Ca^{2+}$. Cell proliferation was monitored in 48-well plates at the times indicated.

DETAILED DESCRIPTION OF THE INVENTION

The subject invention relates to purified naturally occurring factors and novel factors that inhibit cell growth, and to DNA sequences encoding such factors. The invention also relates to the use of inhibitory factor as a research diagnostic or therapeutic agent. Additionally, the invention includes methods of purifying the inhibitory factor of the invention.

Inhibitory factor is an inhibitor of cell division (or cell cycling) of a wide variety of cells including those derived from various tissues of mice, monkey, human, avian and insect species. The factor inhibits cell division in a reversible and nontoxic fashion. It acts by binding a cell surface receptor and causing a variety of intracellular changes including alteration in $Ca^{2+}$ and phosphorylation of key cell regulatory proteins, e.g., the retinoblastoma protein (RB). The term "inhibitory factor" as used herein refers to naturally-occurring inhibitory factors (e.g., natural human inhibitory factor) as well as non-naturally occurring (i.e., different from naturally occurring) factors having amino acid sequences and glycosylation sufficiently duplicative of that of a naturally-occurring inhibitory factor to allow possession of a biological activity of naturally occurring inhibitory factor.

In addition to purified and isolated naturally-occurring inhibitory factors (i.e., purified from nature or manufactured such that the primary, secondary and tertiary conformation, and the glycosylation pattern are identical to naturally-occurring material), the subject invention provides non-naturally occurring polypeptides having a primary structural conformation (i.e., continuous sequence of amino acid residues) and glycosylation sufficiently duplicative of that of naturally occurring inhibitory factor to allow possession of a biological activity of naturally occurring inhibitory factor. Such polypeptides include derivatives and analogs.

One embodiment of the invention is directed to an improved procedures to purify inhibitory factor, and the products of such purification. Although it was thought that the bovine glycopeptide had been purified to homogeneity, sensitive silver-stained gels of the final product exposed the presence of low molecular weight protein contaminants. It was found that the use of ion-exchange column high performance liquid chromatography (HPLC) removes these contaminating protein species and provides a glycopeptide purified to apparent homogeneity without protease activity.

The subject invention includes a method to eliminate the protease activity and to obtain the 18 kDa inhibitory factor in a homogenous form. Such method includes the following steps:

a) conducting mild proteolysis of intact cells or membranes using a protease selected from the group including: pronase, trypsin, chymotrypsin, B substilysin, serine proteases, thiolproteases, cathepsin D proteases, sulphydryl protease, metallo-proteases, trypsin like proteases, estrase and carboxy proteases, non-specific proteases and other specific proteases;

b) conducting DEAE chromatography or preparative isoelectric focussing;

c) conducting lectin affinity chromatography;

d) HPLC size exclusion chromatography; and e) conducting HPLC DEAE chromatography.

The invention also includes a method of purifying the parental 66 kDa protein to apparent homogeneity. Such method includes the steps of:

a) eluting the protein from intact cells or membranes using salt such as NaCl;

b) conducting preparative isoelectric focusing or DEAE chromatography; and c) conducting lectin affinity chromatography.

DEAE chromatography can be performed by batch methods or by using gravity fed or a variety of pressurized columns.

Lectin affinity chromatography can be done in batches or columns using a variety of lectins to either bind the inhibitory factor (for example Limulus polyhemus agglutinin, LPA) or to bind contaminants while leaving inhibitory factor unbound (for example Wheat Germ Agglutinin, WGA). Multiple lectin affinity procedures optionally are substituted for the DEAE or isoelectric focussing.

For purification of recombinant inhibitory factor, the following methods can be used:

Method 1.

Affinity chromatography using specific labels or flags added to the inhibitory factor as a result of the cloning process, and DEAE chromatography Method 2.

Size selection chromatography

DEAE chromatography

The steps listed in either of these procedures are used alone or in combination, depending on purity desired. Lectins are not useful in isolating material grown in E. coli but may be used in isolating materials from hosts capable of glycosylation.

According to another embodiment of the present invention, novel inhibitory factors and DNA and RNA sequences coding for all or part of such inhibitory factors are provided. The present invention includes DNA sequences which include: the incorporation of codons "preferred" for expression by selected nonmammalian hosts: the provision of sites for cleavage by restriction endonuclease enzymes; and the provision of additional initial, terminal or intermediate DNA sequences which facilitate construction of readily-expressed vectors, or production or purification of inhibitory factor.

The present invention also provides DNA sequences coding for polypeptide analogs or derivatives of inhibitory factor which differ from naturally-occurring forms in terms of the identity or location of one or more amino acid residues (i.e., deletion analogs containing less than all of the residues specified for inhibitory factor; substitution analogs, wherein one or more residues specified are replaced by other residues; and addition analogs wherein one or more amino acid residues is added to a terminal or medial portion of the polypeptide) and which share some or all of the properties of naturally-occurring forms. The present invention specifically provides DNA sequences encoding the full length unprocessed amino acid sequence as well as DNA sequences encoding the processed form of inhibitory factor.

Novel DNA sequences of the invention include sequences useful in securing expression in procaryotic or eucaryotic host cells of polypeptide products having at least a part of the structural conformation and one or more of the biological properties of naturally-occurring inhibitory factor. DNA sequences of the invention specifically comprise: (a) DNA sequences encoding inhibitory factor disclosed in Example VII or their complementary strands; (b) DNA sequences which hybridize (under the following hybridization conditions: 2×SSC, 40% formamide, at 37° C., 0.1% SDS, 5×Denharts solution, 0.6 mg/ml yeast tRNA, 10 μg/ml sheared herring sperm DNA, 5.0% polyethylene glycol and 20 mM tris pH 7.5, or more stringent conditions) to the DNA sequences disclosed in Example VII or to fragments thereof; and (c) DNA sequences which, but for the degeneracy of the genetic code, would hybridize to the DNA sequences disclosed in Example VII. Specifically comprehended in parts (b) and (c) are genomic DNA sequences encoding allelic variant forms of inhibitory factor and/or encoding inhibitory factor from other mammalian species, and manufactured DNA sequences encoding inhibitory factor, fragments of inhibitory factor, and analogs of inhibitory factor. The DNA sequences may incorporate condons facilitating transcription and translation of messenger RNA in microbial hosts. Such manufactured sequences may readily be constructed according to the methods well known to those skilled in the art.

According to another aspect of the present invention, the DNA sequences described herein which encode polypeptides having inhibitory factor activity are valuable for the information which they provide concerning the amino acid sequence of the animal (including mammalian) proteins which have heretofore been unavailable. The DNA sequences are also valuable as products useful in effecting the large scale synthesis of inhibitory factor by a variety of recombinant techniques. Put another way, DNA sequences provided by the invention are useful in generating new and useful viral and circular plasmid DNA vectors, new and useful transformed and transfected procaryotic and eucaryotic host cells (including bacterial and yeast cells and mammalian cells grown in culture), and new and useful methods for cultured growth of such host cells capable of expression of inhibitory factor and its related products.

DNA sequences of the invention are also suitable materials for use as labeled probes in isolating human genomic DNA encoding inhibitory factor and other genes for related proteins as well as cDNA and genomic DNA sequences of other mammalian species. DNA sequences are also be useful in various alternative methods of protein synthesis (e.g., in insect cells) or in genetic therapy in humans and other mammals. DNA sequences of the invention are expected to be useful in developing transgenic mammalian species which may serve as eucaryotic "hosts" for production of inhibitory factor and inhibitory factor products in quantity. See, generally, Palmiter et al., Science 222, 809–813 (1983).

In an advantageous embodiment, inhibitory factor is characterized by being the product of procaryotic or eucaryotic host expression (e.g., by bacterial, yeast, higher plant, insect and mammalian cells in culture) of exogenous DNA sequences obtained by genomic or cDNA cloning or by gene synthesis. That is, in an advantageous embodiment, inhibitory factor is "recombinant inhibitory factor." The products of expression in typical yeast (e.g., Saccharomyces cerevisiae) or procaryote (e.g., E. coli) host cells are free of association with any mammalian proteins. The products of expression in vertebrate [e.g., non-human mammalian (e.g., COS or CHO) and avian] cells are free of association with any human proteins. Depending upon the host employed, polypeptides of the invention may be glycosylated with mammalian or other eucaryotic carbohydrates or may be non-glycosylated. Polypeptides of the invention optionally also include an initial methionine amino acid residue (at position −1).

In addition to naturally-occurring allelic forms of inhibitory factor, the present invention also embraces other inhibitory factor products such as polypeptide analogs of inhibitory factor. Such analogs include fragments of inhibitory factor. Following well known procedures, one can readily design and manufacture genes coding for microbial expression of polypeptides having primary conformations which differ from that herein specified for in terms of the identity or location of one or more residues (e.g., substitutions, terminal and intermediate additions and deletions). Alternately, modifications of cDNA and genomic genes can be readily accomplished by well-known site-directed mutagenesis techniques and employed to generate analogs and derivatives of inhibitory factor. Such products share at least one of the biological properties of inhibitory factor but may differ in others. As examples, products of the invention include those which are foreshortened by e.g., deletions; or those which are more stable to hydrolysis (and, therefore, may have more pronounced or longer-lasting effects than naturally-occurring); or which have been altered to delete or to add one or more potential sites for O-glycosylation and/or N-glycosylation or which have one or more cysteine residues deleted or replaced by, e.g., alanine or serine residues and are potentially more easily isolated in active form from microbial systems; or which have one or more tyrosine residues replaced by phenylalanine and bind more or less readily to target proteins or to receptors on target cells. Also comprehended are polypeptide fragments duplicating only a part of the continuous amino acid sequence or secondary conformations within inhibitory factor, which fragments may possess one property of inhibitory factor, (e.g., receptor binding) and not others (e.g., cell inhibitory activity). It is noteworthy that activity is not necessary for any one or more of the products of the invention to have therapeutic utility [see, Weiland et al., *Blut,* 44, 173–175 (1982)] or utility in other contexts, such as in assays of inhibitory factor antagonism. Competitive antagonists are useful in cases of overproduction of inhibitory factor or its receptor.

Of applicability to polypeptide analogs of the invention are reports of the immunological property of synthetic peptides which substantially duplicate the amino acid sequence extant in naturally-occurring proteins, glycoproteins and nucleoproteins. More specifically, relatively low molecular weight polypeptides have been shown to participate in immune reactions which are similar in duration and extent to the immune reactions of physiologically-significant proteins such as viral antigens, polypeptide hormones, and the like. Included among the immune reactions of such polypeptides is the provocation of the formation of specific antibodies in immunologically-active animals. See e.g., Lerner et al., *Cell,* 23, 309–310 (1981) and Ross et al., *Nature,* 294, 654–656 (1981) See, also, Kaiser et al. [*Science,* 223, 249–255 (2984)] relating to biological and immunological properties of synthetic peptides which approximately share secondary structures of peptide hormones but may not share their primary structural conformation.

The present invention also includes that class of polypeptides coded for by portions of the DNA complementary to the protein-coding strand of the human cDNA or genomic DNA sequences of inhibitory factor, i.e., "complementary inverted proteins" as described by Tramontano et al. [*Nucleic Acid Res.,* 12, 5049–5059 (1984)].

Also comprehended by the invention are pharmaceutical compositions comprising therapeutically effective amounts of polypeptide products of the invention together with suitable diluents, preservatives, solubilizers, emulsifiers, adjuvants and/or carriers useful in inhibitory factor therapy. A "therapeutically effective amount" as used herein refers to that amount which provides a therapeutic effect for a given condition and administration regimen. Such compositions are liquids, gels, ointments, or lyophilized or otherwise dried formulations and include diluents of various buffer content (e.g., Tris-HCl., acetate, phosphate), pH and ionic strength, additives such as albumin or gelatin to prevent adsorption to surfaces, detergents (e.g., Tween 20, Tween 80, Pluronic F68, bile acid salts), solubilizing agents (e.g., glycerol, polyethylene glycol), anti-oxidants (e.g., ascorbic acid, sodium metabisulfite), preservatives (e.g., Thimerosal, benzyl alcohol, parabens), bulking substances or tonicity modifers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc. or into liposomes, microemulsions, micelles, unilamellar or multilamellar vesicles, erythrocyte ghosts, spheroplasts, skin patches, or other known methods of releasing or packaging pharmaceuticals. Such compositions will influence the physical state, solubility, stability, rate of in vivo release, and rate of in vivo clearance of inhibitory factor. The choice of composition will depend on the physical and chemical properties of the protein having inhibitory factor activity. For example, a product derived from a membrane-bound form of inhibitory factor may require a formulation containing detergent. Controlled or sustained release compositions include formulation in lipophilic depots (e.g., fatty acids, waxes, oils). Also comprehended by the invention are particulate compositions coated with polymers (e.g., poloxamers or poloxamines) and inhibitory factor coupled to antibodies directed against tissue-specific receptors, ligands or antigens or coupled to ligands of tissue-specific receptors. Other embodiments of the compositions of the invention incorporate particulate forms protective coatings, protease inhibitory factors or permeation enhancers for various routes of administration, including parenteral, pulmonary, nasal, topical (skin or mucosal) and oral.

The invention also comprises compositions including one or more additional factors such as chemotherapeutic agents, TNF, cytokines (e.g., interleukins), antiproliferative drugs, 5FU, alkylating agents, antimetabolites, and drugs which interfere with DNA metabolism.

In another embodiment, inhibitory factor is administered in conjunction with radiotherapy.

Polypeptides of the invention may be "labelled" by association with a detectable marker substance (e.g., radiolabeled with $^{125}$I, enzyme labelled, or biotinylated) to provide reagents useful in detection and quantification of inhibitory factor or its receptor bearing cells in solid tissue and fluid samples such as blood, urine, cerebral spinal fluid or culture media.

The subject invention also relates to antibodies specifically binding inhibitory factor. One embodiment is polyclonal antibodies which bind inhibitory factor but not any proteases. A further embodiment of the invention are stable hybridomas, i.e., hybridomas capable of being passaged repeatedly and cryopreservation, such hybridomas producing antibodies specifically binding inhibitory factor. In contrast to conventional antibody (polyclonal) preparations which typically include different antibodies directed against different determinants (epitopes), each monoclonal antibody is directed against a single determinant on the antigen. Monoclonal antibodies are useful to improve the selectivity and specificity of diagnostic and analytical assay methods using antigen-antibody binding. Also, both monoclonal and polyclonal antibodies are used to neutralize or remove inhibitory factor from serum or from culture media or other liquids. A second advantage of monoclonal antibodies is that they can be synthesized by hybridoma cells in culture, uncontaminated by other immunoglobulins. Monoclonal antibodies may be prepared from supernatants of cultured hybridoma cells or from ascites induced by intraperitoneal inoculation of hybridoma cells into mice. The hybridoma technique described originally by Kohler and Milstein [*Eur. J. Immunol.* 6, 511–519 (1976)] has been widely applied to produce hybrid cell lines that secrete high levels of monoclonal antibodies against many specific antigens.

Applications of the Inhibitory Factor of the Invention

The nontoxic and reversible nature of the cell cycling inhibition by the polypeptide of the invention permits many applications.

A) Synchronization of Cells

The inhibitory factor of the subject invention is useful as a reagent to synchronize cell populations in culture for studies including, but not limited to, measuring specific biochemical events in specific stages of the cell cycle, receptor-ligand interactions that influence cell division, drug effects, effects of viruses, effects of transforming agents, effects of mutagens, and effects on the ability of cells to fuse with other cells or react to environmental stimuli (heat, cold, etc.), and signal transduction events that occur subsequent to receptor-ligand interaction. The inhibitory factor is useful in studies with cells derived from mammalian and non-mammalian species, primary cultures and established cell lines and nontransformed and suitable tumorigenic cell lines.

i) Exponentially Dividing Cell Cultures.

The inhibitory factor is useful for examining various stages of the cell cycle. Adding, e.g., 1 to $10 \times 10^{-8}$M of the inhibitory factor to exponentially dividing cell cultures, and incubating the cells for a period of time, allows all cells to come to arrest at one point in the cell cycle. Long incubation (over one generation time) provides the largest percentage of arrested cells. The incubation time varies according to the application. The inhibitory factor-containing medium is then removed or inactivated (e.g., using antibodies), (removing the media and replacing it will effect removal of inhibitory factor), and the cells are allowed to proceed through the cell cycle. By timing the period of experimental intervention, various stages of the cell cycle can be examined for virtually all metabolic events of interest. For comparative reasons, several types of control cultures are used containing: 1) control cultures never exposed to inhibitory factor; 2) control cultures with inhibitory factor not removed or deactivated; and 3) control cultures refed with media containing inhibitory factor. Synchronized cultures will provide greater magnitude effects in evaluation of a large number of environmental, pharmocologic or other stimuli.

ii) Cell Cycle Arrested Cultures.

The polypeptide of the subject invention is useful for studying metabolic events of cells and effect of growth stimulators on confluent cells (density inhibited cells). Mitogens are added to non-growing cells to stimulate division of the cells and inhibitory factor e.g., 1 to $10 \times 10^{-8}$M is added at the same time or at various times after the mitogens. Various metabolic events including, but not limited to, DNA synthesis, RNA synthesis, protein synthesis and posttranscriptional and posttranslational modifications of macromolecules can be studied as related to mitogen stimulated cell cycling. In addition, this method offers a novel method to study the potential interactions between the inhibitory factor and various mitogenic substances.

iii) Other Cultures

Primary explants or cultures of tumors or some other cultures which are not in exponential growth or stable (confluent) state can be treated with inhibitory factor.

CYTOGENETIC APPLICATIONS

Unlike other methods of synchronizing cells (such as mitotic shake off or drug treatments) inhibitory factor synchronizes the vast majority of the cells in a culture. Inhibitory factor treated cells do not divide until approximately ten hours after removal of inhibitory factor; then, within one hour, greater than 95% enter and successfully complete mitosis, resulting in a striking doubling of cell number. This contrasts with the effects of currently used mitogens to stimulate division, for example following the stimulation of lymphocytes with PHA the number of mitosis gradually rises beginning at 40 hours, reaches a maximum and levels off at approximately 3% after 72 hours (Verma et al. *Human Chromosomes*, Pergamon Press, N.Y., N.Y. (1989)). Inhibitory factor reversibly inhibits over 90% of cultured human products of conception cells and cultures of many types of cancer cells.

The time course of inhibitory factor effect is consistent with knowledge of cell cycle transition times (Stubblefield, Methods Cell Phys. 3,25–44, 1968): S lasts 6–9 hrs, G2 lasts 2 to 5 hrs and M can take from twelve to 60 minutes.

While inhibitory factor appears to halt the cells at a single highly discreet point in late G1/GO (Fatteay et al., supra 1991) most arresting agents cause cells to grind to a halt when they run out of DNA precursors sometime in S. A higher degree of synchrony will be achieved using inhibitory factor. The experimental data shows a very sharp increase in cell numbers and preservation of synchrony for more than one mitosis, a highly unusual property. In light of the natural occurrence of the molecule in normal human tissues, the natural occurrence of its receptor, and the reversibility of inhibition, synchronization by inhibitory factor is less toxic than currently available methods.

The use of inhibitory factor is expected to greatly increase the number of mitoses compared to untreated cells and even compared to cells subject to a typical metaphase block of a few hours, or PHA. Optionally, this method is used in combination with traditional metaphase blockers (e.g., Colcemid). This is especially important in solid tumors where the cells have a variety of doubling times. The use of the inhibitory factor along with metaphase blockers allows the convenient simultaneous collection of cells with different doubling times.

Inhibitory factor is useful for obtaining different groups of mitotic figures that represent subpopulations of cells with different rates of growth. This occurs since the cells with the most rapid S phase enter mitoses before cells with a longer S phase. These cells are preferentially observed or isolated. Similarly cells with various length S phases can be isolated or observed. An easy way of observing such cells is with metaphase spreads and an easy way of isolating such cells is by shaking off the mitotic cells from the culture vessel.

If an additional generation is allowed to proceed before isolation or observation, differences in the length of M and especially G1 can also be noted.

B) Inducing Differentiation

The inhibitory factor is useful to experimentally induce cellular differentiation and the subsequent morphological and biochemical alterations that accompany this process. This includes cells obtained from solid and fluid tissues from mammalian and non-mammalian species.

Various cells in culture are treated with, e.g., 1 to $10 \times 10^{-8}$M of the polypeptide inhibitory factor, and/or its peptide fragments and events associated with cellular differentiation, including but not limited to specific metabolic processes and morphological changes, are monitored during the culture period. In vivo differentiation is useful to treat various types of cancers and other diseases (see below).

Inhibitory factor is useful in the treatment of diseases where differentiation of nervous system cells is needed. The factor is also useful in enhancing nerve tissue repair.

C) Arresting the Cell Cycle

The inhibitory factor provides cell cycle arrest and cultures in "suspended animation" that subsequently permits an investigator to store the cultures without routine and laborious refeeding or subculturing the cells on as frequent a schedule.

This application also provides a means to maintain cell cultures in "suspended animation" for purposes associated with shipping the cells over long distances, or maintaining the cultures outside of the culture facility for extended periods of time, without routine refeeding or exchanging cell culture medium. It can be especially difficult to refeed or perform maintenance or cells being prepared for transport to space or a large number of clones being analyzed for function. Embryos, fetuses and adult organisms can similarly be caused to suspend division temporarily by use of inhibitory factor.

D) Treatment of Neoplastic Disease

The first embodiment of the invention for treatment of neoplastic diseases (e.g., carcinomos, melanomas, sarcomas, lymphomas, adenomas) is the direct treatment to effect improved clinical state. Inhibitory factor may be used alone or in combination with drugs to directly slow or stop unwanted proliferations. Drugs most useful in combination with inhibitory factor to stop cancer cells are those that work throughout the cell cycle such as alkylating agents which inhibit glycolysis and respiration as well as effecting DNA. Examples of these are Busulfan, Chlorambucil, Cyclophosphamide, Dacarbazine, Mechlorethahamine, Melphalan and Thiotepa. Certain antitumor antibiotics such as the anthracycline and chromycins (Dactinomycin, Daunorubicin, Doxorabicin, Placamyccin, Mitomycin C) and the nitroureas and cytokines which are cell cycle nonspecific may similarly be used in combination with inhibitory factor to cause direct toxicity.

Cancers are particularly dangerous because the cancerous cells continue to proliferate and often metastasize (spread to and proliferate at distant sites). In general, "undifferentiated" or "embryonic" or "primitive" cells within the cancer are the most likely to proliferate and spread. Cancers that spontaneously regress often do so by undergoing differentiation. In addition, successful therapy often induces differentiation. Worsening of the disease in contrast is associated with emergence of less differentiated cells. Pathologists routinely use greater degrees of differentiation as a good prognostic indicator and find more poorly differentiated tumors to the most aggressive. Thus, differentiation is good for the patient. Teratocarcinoma, ovarian carcinoma, thyroid carcinoma, neuroblastoma, glioma, melanoma, lymphomas, leukemias, prostrate cancer, colon cancer, breast cancer, lung cancer and other cancers all behave in this manner. In virtually all cancers the level of differentiation is an important factor, in the cases mentioned above, it is a critical factor.

Animal cancers (including human cancers) are subject to inhibitory factor therapy by causing differentiation. An example of this is the differentiation and permanent irreversible inhibition of the human leukemia line H6-60 by inhibitory factor.

Inhibitory factor may be used in combination with known chemotherapy, as well as on its own to cause difffferentiation. Certain drugs are known to act by stimulation differentiation and slowing the growth of tumor cells. These includes androgens, estrogens, steroids and some cytokines. Inhibitory factor may be advantageously combined with drugs like Tamoxifin, Estradiol, Ethynl Estradiol, Diethylstibesterol, Premarin, Medrooxy progesterin, Megestrol, Hydroxyprogesterone, Testosterone, Floxymestrone, Methyl testosterone, Testolactone and other androgens, and corticosteroids including Predsinsone, Hydroxycortisone and Dexamethasone to stimulate differentiation and slow tumor growth.

Even if the cancer is not forced to differentiate by inhibitory factor but is forced to remain in a nondividing state major clinical effect can occur due to the halting of disease progress and prevention of further metastasis. The body's natural immunity may act to destroy cancers that are no longer growing.

A second example of application in the class of direct therapy is treatment of any skin or squamous cancer or overproliferation of skin cells. It has been found that some cells—human keratinocytes—are especially sensitive to inhibitory factor. Basal Cell Epithelioma's (BCE), squamous carcinomas and a wide variety of proliferative skin lesions including various icthyosis and psoriasis are all treatable with inhibitory factor. Other proliferative diseases which are treated with inhibitory factor include easinophilia, benign reactive lymphocylic hyperplasia, lymphoproliferative diseases, adenomas and certain preneoplastic lesions like familiar polyposis.

Inhibitory factor is useful in the treatment of human and animal leukemic disease (feline leukemia, HTLV virus, etc.).

The second embodiment of the invention to treat proliferative lessions (either concerns or benign proliferations) is in combination with other drugs. The above diseases and other diseases may be treated thusly. It has been demonstrated that in vitro inhibitory factor acts in a synergistic manner with other cell modulators For example preliminary experiments (Woods, et al., FASEB J, 5: 1463, 1991) have shown that inhibitory factor increases TNF cytotoxicity to certain tumor cells.

Other applications involve the inhibitory factor as adjuvant to increase the sensitivity of neoplastic cells to other agents. This permits the use of lower concentrations of anti-neoplastic agents to provide effective doses at less toxic levels.

Application is also be found in the use of the inhibitory factor in multiple-drug therapy for neoplastic disease. The inhibitory factor augments the efficacy of treatment by other compounds by a molecular mechanism that is separate but synergistic. This application is equally appropriate for both human and veterinary medicine. Inhibitory factor can be used alone or with one or more additional factors such as TNF and cytokines in the treatment of disorders.

The administration of inhibitory factor with other agents such as one or more other factors, is temporally spaced or given together. The route of administration may be intravenous, intraperitoneal sub-cutaneous, intramuscular, topical, oral or nasal.

A third embodiment of the invention relating to the use of inhibitory factor as a chemoprotectant for normal cells in combination with chemotherapy agents. This combination decreases side effects. It is dependent on the cancer being resistant to inhibitory factor. Since inhibitory factor 1) prevents Rb phosphorylation; 2) underphosphorylated Rb maintains cells in a quiescent state; 3) certain cancer cells have oncogene producers which complex Rb; and 4) complexed Rb is not be effected by inhibitory factor. Certain tumors are insensitive to inhibitory factor. Cell lines transformed with SV40 large T antigen were assayed for inhibition by inhibitory factor. These cells were not inhibited by inhibitory factor. Similarly, human fibroblasts transformed with Adenovirus are not inhibited. Control 3T3 cells used in these experiments were inhibited as in previous presented experiments. All three of the cell lines chosen because they contain Rb binding oncoproteins were found to resist inhibition, while none of the randomly chosen lines previously screened were resistant. Prostate cancer, bone cancer and bladder cancer are examples of cancer types insensitive to inhibitory factor. Similarly, in treatment of cancers derived from lung, breast, immune cells, blood cells, or other cells, inhibitory factor acts as a chemoprotectant. Other mechanisms of resistance are also possible.

In the presence of inhibitory factor, human cancer cells not inhibited by inhibitory factor, can be killed by a variety of treatments that destroy dividing cells while normal cells which are reversibly inhibited by inhibitory factor would be protected from destruction. Thus inhibitory factor is very useful as a drug to decrease the side effects of chemotherapeutic agents. It is given along with or just prior to cytotoxic therapies. The normal cells would respond to inhibitory factor by stopping in a physiologically "safe" G1 resting phase while the cancer cells would continue to grow and be susceptible to killing by cytotoxic agents such as drugs or radiation.

Certain drugs are known to specifically efffect cells in M or G2 phase of the cell cycle. These include Zinostatin Bleomycin and some other anti-tumor antibiotics. In addition, the alkyloids such as vinblastin, vincristine, vindesine and others specifically act in M phase by blocking microtubule action. The Epipodophyllotoxins, etoposide and teniposide also specifically act in M phase with some effect in G2 and S. The antimetabolites such as Fluorouracil, Floxurridine, Cytarabine, purine antagonist (mercaptopurine, 6 thioguanine, azathioprine) and folate antagonist (methotrexate, dichloromethotrexate, triazinate), hydroxurea and hexamethylmelamine are also S sphase specific. Inhibitory factor which will keep cells in G1 and specifically chemoprotect the normal against the toxicity of agents in these classes.

The specific cancers which may be best treated in the combination with certain drugs are evident from previous knowledge of the mode of action of these drugs and the cancers against which they are effective see, for example, The Washington Manual 1989, Dept. of Medicine, Washington University.

Certain dangerous DNA viruses are believed to interfere with cellular control mechanisms by producing molecules that interact with RB or with other cell regulatory molecules controlled by phosphorylation or by mechanisms affected by inhibitory factor (e.g., p53 or cyclins). It is believed that certain types of Human Papilloma Virus play a major role in causing cervical cancer. Carcinogenic types of Human Papilloma Virus (HPV types 16 and 18) produce proteins inactivating RB (Dyson, et al., 1989) (similarly to cells transformed with Adeno E1A or SV40 large T). This invention includes assays to determine if certain tumors have affected the RB mechanism, and the use of inhibitory factor as a protectant during therapy of these tumors.

In the case of preneoplastic (dysplastic) mucosal lesions or in situ carcinoma caused by HPV, a combination of inhibitory factor to protect adjacent normal tissue and a cytotoxic agent is useful for treatment. Such combinations can be locally applied. Current treatments are various surgical procedures which tend to leave some in situ cancer behind unless relatively large areas are removed.

Inhibitory factor without cytotoxic therapies are effective against the condyloma (wart) producing viruses that do not produce oncogene products reactive with RB (e.g., HPV Types 6/11, Dyson, et al., Science 243, 934–937, 1989).

E) Screening Antineoplastic Agents

The inhibitory factor (which provides mitotic arrest) has application in screening of drugs. Many drugs act specifically in one region of the cell cycle (see above). By comparing the putative anti-cancer drugs effect on parallel sets of cultures—one set proliferating and the other mitotically arrested with inhibitory factor—the relative action on stable versus multiplying populations is readily assessed. Since the mitotic arrest mediated by the polypeptide is totally reversible, future growth measured by colony formation as well as survival of inhibitory factor treated cells is easily assessed. Drugs which act at other specific stages of the cell cycle can also be advantageously sought and analyzed using inhibitory factor. Inhibitory factor is used to place cells in a specific stage of the cell cycle as described in section A) above.

ABNORMAL PROLIFERATIVE STATES.

Inhibitory factor is also useful in the treatment of other diseases having abnormal proliferation such as psoriasis, other icthyosis, keloid or certain autoimmune diseases. Keratinocytes are especially susceptible to inhibitory factor. Inhibitory factor is useful in the treatment of psoriasis, keloids and other proliferative skin diseases.

Psoriasis

Psoriasis results from the excess division of skin cells (as do other proliferative skin diseases called "icthyosis"). In patients with psoriasis, skin cells divide seven times faster than normal. This disorder is treatable with inhibitory factor.

Warts

Warts (or "condyloma") also are the result of excess epthelial cell proliferation, as are several other skin pathologies. Warts are caused by Human Papilloma Viruses (HPV's). Since it is known that keratinocytes (the type of epithelial cells that overproliferate in these lesions) are especially sensitive (approximately 30–50 fold more sensitive than most cells) to inhibitory factor these lesions can be treated effectively with inhibitory factor.

Keloid

Keloid is a disease caused by overproliferation of scar tissue, thus it also can be advantageously treated with inhibitory factor as it is known that human fibroblasts are inhibited.

Atherosclerosis

Atherosclerosis involves the overproliferation of cells lining the blood vessels. Inhibitory factor reversibly prevents proliferation of such cells including smooth muscle cells and endothelial cells. Overproliferation leads to a variety of abnormalities including heart disease, strokes, renal disease and others. These diseases also can be prevented by decreasing atherosclerosis with inhibitory factor.

Proliferative Disease of the Eye

Proliferative diseases of the eye including retinopathy are treatable with inhibitory factor to stop unwanted proliferation.

Inflammatory Disorders

Unwanted inflammatory states, such as allergies and autoimmune disease, even some types of arthritis involve the proliferation of certain cells that can be stopped with appropriate inhibitory factor therapy. Multiple sclerosis has been postulated to be either a viral or autoimmune (inflammatory disease). In either case TNF is known to be altered locally in M.S. and thus inhibitory factor can be used as therapy.

Aging

It is believed that normal human cells have a limited capacity to divide. After a certain number of divisions this capacity is exhausted and the human body becomes unable to replenish itself. This is supported by evidence including the fact that cells from a young person will divide many times in tissue culture before "senescence" (failure to divide) while cells from an older person have a much more limited capacity to divide before senescence. The use of inhibitory factor early in life to prevent unnecessary divisions might allow some of the limited number of divisions to be saved for old age and thus to delay the onset of various organ degenerations seen in old age. This includes use as an ointment for skin aging as well as by other means to prevent deterioration of various internal tissues.

EUCARYOTIC CELL CLONING.

Temporary inhibition by inhibitory factory factor might also be extremely useful in situations where cell passages are difficult. For instance in eucaryotic cell cloning often a large number of clones are initially obtained but only a few will be useful. Growth and passage of many clones during the evaluation period (for example while assays of the clone's ability to produce a biologic material, e.g., a monoclonal antibody, a biologic response modifier or an enzyme of interest) may be difficult. Inhibitory factor can be used to easily place cells in a safe but non-dividing state. This method preserves a much larger number of important clones during the evaluation period with less effort and chance of loss or contamination.

Production of Cell Products

Inhibitory factor reorients the protein synthetic mechanism of cells; initially it shuts off the synthesis of many proteins (total synthesis drops by 80%) however within hours the total synthesis is only 20% to 25% less than in exponentially growing cells. Thus, it is believed that certain structural proteins necessary for an increase in cell number are shut off but many proteins made in G1 are actually synthesized at a higher rate. Thus increased production of certain biologically useful proteins (e.g., monoclonal antibodies or other excreted proteins) is possible using inhibitory factor. Inhibitory factor increases production of monoclonal antibodies. Even if production per cell is not increased it may be very beneficial to have a metabolically active "bioreactor" with stable cell number in many instances. In theory, such bioreactors might even provide an entire metabolic pathway.

Diagnostic Testing

Inhibitory factor is helpful as an aid in karyotypic (chromosome) analysis. It is especially important in situations where low numbers of mitotic cells are present, such as solid cancers, or in situations where low numbers of cells are available for analysis (some difficult amniotic fluid taps or the isolation of sub populations of cells).

Isolation of Viruses

Additionally, the inhibitory factor is useful in isolating viruses. Viruses often require actively dividing cells. The most frequent reason for in laboratory failure to isolate viruses from adequate clinical specimens in plating of the virus on cells that have become too dense or too confluent. Overgrown cells are also the major cause of delay in isolation of viruses clinical labs most frequently isolate. Inhibitory factor can be used to hold cells at the ideal density for virus growth and then initiating exponential growth (which is most helpful for growing viruses such as herpes virus, cytomegulovirus and many other viruses which require actively growing cells) by removing inhibitory factor as described above.

Some viruses are difficult to culture using current methods. However, if cells were infected at the optimum point in the cell cycle, for example, during S phase or M phase or G2 growth is much more reliable. The only methods currently available to achieve cultures with high amounts of S, M or G2 phase cells for this or any purpose is inhibitory factor.

Lastly is the use of inhibitory factor to allow growth of viruses which cannot currently be grown in the lab (e.g., HPV). It is believed that HPV and other viruses requires cells with certain differentiation properties. Since inhibitory factor will cause differentiation, it can facilitate growth of this class of viruses.

Yeast

The use of yeast cultures offers a rapid and economical assay for routinely measuring inhibitory factor activity. Inhibition can readily be measured within a few hours and an entire kinetic experiment can be conducted in a single tube containing 100 $\mu$l or less of medium.

The sensitivity of yeast organisms to the inhibitory factor opens a wide variety of genetic and molecular studies not available with mammalian cell lines. There are a multitude of yeast strains with well-characterized mutations associated with cell cycle regulation that offer an unusual opportunity to study the molecular biology of inhibitory factor action.

The apparent cytotoxicity to yeast at the higher concentrations of the inhibitory factor presents new chemotherapeutic uses of the inhibitory factor in treating yeast infections in normal individuals as well as individuals who are immune-compromised (i.e., AIDS patients, organ transplant patients, etc.).

Nucleic acid products of the invention are useful when labeled with detectable markers (such as radiolabels and non-isotopic labels such as biotin) and employed in hybridization processes to locate the human inhibitory factor gene position and/or the position of any related gene family in a chromosomal map. They are also useful for identifying human inhibitory factor gene disorders at the DNA level and used as gene markers for identifying neighboring genes and their disorders. The identification of the genes and defects in them are important in diagnosis and prognosis of proliferative diseases and cancers. The protein from these genes is assayed by use of monoclonal or polyclonal antibodies in various formats including western blots, dots blots and ELISAs. The detection of protein facilitates diagnosis and prognosis of various diseases involving altered levels of cell proliferation.

Typically, to affect cells inhibitory factor should be administered in a range of 1 nanomolar to 1 micromolar, advantageously the factor is administered at a concentration from 1 to $10 \times 10^{-8}$ molar.

Other components of the media affect the optimal concentration of inhibitory factor: for example, media with low calcium concentration increases the sensitivity to inhibitory factor.

The following examples are offered to more fully illustrate the invention, but are not to be construed as limiting the scope thereof.

THE EXAMPLES

Example I

Isolation and Purification of the 18 kD Bovine Glycopeptide

A suspension of bovine cerebral cortex cells was prepared in Dulbecco's minimal essential medium (DMEM) containing 25 mM HEPES buffer (pH 7.1). The cells were pelleted by centrifugation at 2000×g for 5 min, the cell pellet was suspended in HKM buffer (10 mM HEPES, 120 mM KCl, 5 mM $MgCl_2$, pH 7.1) and incubated with 0.02 units/ml of proteinase from S. griseus ("pronase") for 15 min at 37° C. with constant mixing.

Previous reports suggested a single treatment with the protease was sufficient (Sharifi et al., Neurochem. 46: 461–469, 1986a), however, three subsequent protease treatments of the bovine cerebral cortex cells essentially triples the yield of the sialoglycopeptide inhibitory factor released.

The cells were then removed by centrifugation at 2000 g for 5 min. The supernatant fluids containing released molecules were then collected, the macromolecules were precipitated with ethanol overnight, and the resulting precipitate was collected by centrifugation, resuspended in 100 ml distilled water, extracted with chloroform/methanol (2:1, v/v), dialyzed against four liters of distilled water overnight, with at least six water changes, and the dialysate was then lyophilized to dryness.

The lyophilized material was resuspended in 2 ml of 0.05M acetate buffer (pH 5.0), clarified by three subsequent centrifugations at 1,000 g for two minutes and applied to a DEAE-agarose gel. Approximately 50 mg protein of the chloroform/methanol-extracted material was incubated with DEAE-agarose gel (10 ml bed volume) at 4° C. for 30 min with constant mixing. The gel was washed three times with 3 ml of the acetate buffer and the biological inhibitory factor was eluted with 3 ml of 0.4M NaCl in 0.05M acetate buffer (pH 5.0). The eluate was then dried in a Savant speed-vac apparatus.

To increase the yield of inhibitor obtained from each lyophilized sample, the material that elutes from the DEAE-agarose column is recycled to a fresh DEAE-agarose column and again eluted with 0.4M NaCl in 0.05M acetate buffer (pH 5.0) as described above. Alternatively, one can increase the size of the original DEAE-agarose bed volume to approximately 25 ml. Either of these approaches increases the yield of inhibitory factor by approximately 2-fold.

The DEAE-agarose purified samples were then further purified with agarose-bound wheat germ agglutinin (WGA). The WGA was previously equilibrated with phosphate buffered saline (PBS, pH 7.1), and the protein fraction was suspended in 1.5 ml of PBS and applied to a 1.0 ml WGA column. After incubation at 4° C. for 30 minutes, the inhibitory factor-containing fraction that does not bind to the WGA column was removed by washing with 2 ml of PBS.

The WGA-eluted fraction was then further purified by applying the protein to a HPLC TSK-3000 size exclusion column. The elution buffer consisted of 0.1M sodium phosphate (pH 6.8), and the flow rate was adjusted to 0.1 ml/min. The eluate was monitored for absorption at $A_{280}$, and the fractions associated with the major protein peak were pooled, dialyzed overnight at 4° C. against four liters of dilute PBS. The sample was then dried in a speed-vac apparatus, resuspended in 0.5 ml of distilled water and the protein content and the biological inhibitory activity were measured.

Example II
Measurement of the Biological Inhibitory Properties of the Inhibitory Factor i) Protein Synthesis Inhibition Protein synthesis was measured with cells from subconfluent cultures that were suspended in DMEM containing 25 mM HEPES buffer, pH 7.1 (Sharifi et al., Neurochem. 46: 461–469, 1986a; Bascom et al., J. Cell Physiol. 128: 202–208, 1986). Either HKM buffer alone (controls), or HKM buffer with various concentrations of the 18 kD brain inhibitory factor (experimentals) were added to each reaction tube. The cells were incubated for 30 to 45 min at 37° C. to allow the cells to bind the inhibitory factor, $^{35}$S-methionine in HKM was then added to radiolabel cellular proteins and the cells were incubated at 37° C. for an additional 10 to 30 min. After this incubation period the macromolecules were precipitated with trichloroacetic acid (TCA) and the amounts of intracellular acid-soluble and acid-insoluble radioactivity were determined by scintillation counting. This assay is rapid and requires only nanograms of inhibitor, and one unit of biological activity is set as the quantity that provides a 25% inhibition of mouse 3T3 cell protein synthesis.

ii) DNA Synthesis Inhibition $^3$H-thymidine incorporation was measured with cultures in 24- or 48-well culture plates. For experiments on mitotic arrest and cell cycle kinetics, subconfluent cell monolayers were incubated with 0.2 ml of DMEM medium containing 2.5% calf serum and 3H-thymidine (adjusted with non radioactive thymidine to a specific activity of 0.5 Ci/mmole) for 2 hr at 37° C. After incubation the media were removed and the cells were solubilized in 1 ml of 0.2N NaOH. Macromolecules were precipitated with 10% TCA, after the addition of 0.1 ml of 1% BSA as a carrier. Radioactive thymidine in the intracellular acid-soluble pools and in the cell DNA was measured by scintillation counting (Chou et al., Cancer Lett. 35: 119–128, 1987; Fattaey et al., J. Cell. Physiol. 139: 269–274, 1989).

Experiments where the sialoglycopeptide was studied as a potential antagonist to mitogens, that stimulate cell division, (e.g., EGF, TPA and bombesin) utilize confluent and quiescent cultures (See Bascom et al., J. Cell. Biochem. 34: 283–291, 1987; Chou et al., Cancer Lett. 35: 119–128, 1987; Johnson and Sharifi, Biochem. Biophys. Res. Comm. 161: 468–474, 1989).

iii) Cell Growth Inhibition

Cells were plated in 48-well tissue culture plates at a density of 2 to $5 \times 10^3$ cells per well and the cultures were incubated for ~4 hr prior to initiating growth-inhibition experiments. Cultures were refed with filter-sterilized medium at the start of the experiment, either with 0.5 ml of complete medium alone (controls) or with 0.5 ml of complete medium containing various concentrations of the glycopeptide inhibitory factor (experimentals) (Fattaey et al., J. Cell. Physiol. 139: 269–274, 1989; Fattaey et al, Exper. Cell Res. 194: 62–68, 1991; Edson et al., Life Sci. 48: 1813–1820, 1991).

Triplicate samples were taken at least once every generation time (18 to 24 hr), and cells were harvested by trypsinization, washed, dissociated by gentle pipetting, and counted in a 1:20 dilution of Isoton II in a Coulter Counter.

A remarkable property of inhibitory factor is that it is active on a wide range of target cells. These cells include fibroblast and epithelial cells, non-transformed cells and many transformed cells, obtained from diverse species ranging from humans to insects. (See below).

SENSITIVE TARGET CELL RANGE OF THE INHIBITORY FACTOR

| Cell | Species | Cell-Type | Transformed or Nontransformed |
|---|---|---|---|
| Swiss 3T3 | mouse | fibroblast | nontransformed |
| Balb/c 3T3 | mouse | fibroblast | nontransformed |
| Balb/c-MK* | mouse | keratinocyte | nontransformed |
| C50** | mouse | keratinocyte | nontransformed |
| 308** | mouse | keratinocyte | transformed |
| PdVC57** | mouse | keratinocyte | transformed |
| Kidney | mouse | primary | nontransformed |
| Embryo | mouse | primary | nontransformed |
| N2a | mouse | neuroblastoma | transformed |
| N-18 | mouse | neuroblastoma | transformed |
| 1316 | mouse | fibrosarcoma | transformed |
| 2247 | mouse | fibrosarcoma | transformed |
| 2237 | mouse | fibrosarcoma | transformed |
| HSBP | human | fibroblast | nontransformed |
| HUV-EC-C | human | endothelial | nontransformed |
| IMR-90 | human | diploid fibroblasts | nontransformed |
| WI-38 | human | diploid fibroblasts | nontransformed |
| IMR-32 | human | neuroblastoma | transformed |
| HL-60[1] | human | myeloid leukemia | transformed |
| HFK | human | keratinocyte | nontransformed |
| U20S | human | osteosarcoma (RB$^+$) | transformed |
| T98G | human | glioblastoma | transformed |
| MDBK | bovine | epithelial-like | nontransformed |
| NRK-52E | rat | epithelial-like | nontransformed |
| A7r5 | rat | smooth muscle (aorta) | nontransformed |
| PC-12 | rat | pheochromocytoma | transformed |
| BSC-1 | monkey | epithelial-like | nontransformed |
| CE | avian | fibroblast | nontransformed |
| C$_4$#1 | avian | spleen | transformed |
| MSB | avian | T cells | transformed (Marek's) |
| PI-5.4 | insect | embryo (Indian meal moth) | nontransformed |
| Sf9 | insect | ovary (armyworm) | nontransformed |

*>30-times more sensitive to the inhibitory factor
**~100-times more sensitive to the inhibitory factor
All other cell lines were arrested in a reversible manner with 3 to $8 \times 10^{-8}$ M inhibitory factor
[1]Irreversibly arrested by the inhibitory factor which induces terminal differentiation.

Example III
Improved Purification, and the Elimination of the Protease Activity by the Addition of a Final HPLC Ion-Exchange Step Although the purification procedure described in Example I appears to provide a 18 kDa glycopeptide product that was homogeneous, small molecular weight peptides contaminated the samples to various degrees from preparation to preparation. These contaminants were difficult to visualize when purified samples of the glycopeptide were analyzed by SDS-polyacrylamide gel electrophoresis (SDS-PAGE) and stained by the Comassie Blue method of Sasse et al., in Current Protocols in Molecular Biology, (F.A. AuSabel, R. Brent, R. E. Kingston, D. D. Moore, J. G. Saidman, J. A. Smith and K. Struhl, eds.), pp. 10.6.1–10.6.2 (1991). When the gels were stained by the silver-stain method of Merril et al., Methods Enzymol. 104: 441–447 (1984), the presence of the contaminating peptides could be seen as light and diffuse stained areas, often masked by the tracking dye used to time the electrophoresis run, and in the area of the SDS-PAGE sample representing contaminating molecules of 14 kDa or smaller. Careful washing and destaining is necessary to reveal this smear. Depending on the particular glycopeptide preparation being analyzed, the relative amount of small molecular weight peptide contamination varied from 20% to 40% of the total glycopeptide product (determined by densitometric scanning of the silver-stained gels).

The presence of these small molecular weight peptides reduced the specific biological inhibitory activity (units per nanogram) and prevented meaningful studies concerning structural analysis and protein sequencing of the glycopeptide inhibitory factor.

A simple, but effective, procedure was developed to provide a homogeneous glycopeptide preparation. This procedure involves the use of a HPLC/DEAE ion-exchange step as the final step of bioseparation.

A Protein-Pak DEAE (Waters) HPLC column was equilibrated with 20 mM Tris-HCl (pH 8.2) or 40 mM $NH_4HCO_3$ (pH 8.0) and 10 mM NaCl. The glycopeptide (20 to 60 micrograms) was added to the DEAE column and the glycoprotein was eluted by introducing over a 30 minute period a linear NaCl gradient that increased from 10 to 100 mM. The eluant was monitored at $A_{280}$, and the purified glycopeptide that eluted from the HPLC column as a single and sharp peak, at approximately 50 mM NaCl (as determined by refractometry), and well-separated from the contaminating small molecular weight peptides, was collected manually.

The glycopeptide inhibitory factor was then lyophilized to dryness and resuspended in 2.0 ml of distilled water. The sample was then desalted by five serial centrifugations (each with 2.0 ml of distilled water) in microconcentrators (Amicon) fitted with a membrane that retained molecules over 10 kDa. The retentate, containing the 18 kDa glycopeptide was lyophilized and stored frozen at −70° C.

Analysis of the final glycopeptide inhibitory factor product by silver-stained SDS-PAGE gels stained by the silver method revealed a single 18 kDa protein band that had been successfully resolved from the contaminating small molecular weight peptides.

The improved procedure for purification yielded a homogeneously purified glycopeptide that was free of any detectable protease activity, thereby providing preparation for structural analysis and protein sequencing. It also provides a product with a single mode of action due exclusively to inhibitory factor.

Example IV
Amino Acid Sequence Analysis

Sequencing was attempted using the general procedures set forth in Lane et al, J. Protein Chem. 10 No. 2, 151–160 (1991).

Sequencing Procedures Strategy

A 12 microgram (600 pmoles) of inhibitory factor was prepared as in Example I and further purified as in Example III. Since the protein is both N-terminally blocked and glycosylated, sequencing and associated tasks were extremely difficult.

Cyanogen bromide was obtained from Sigma, sequencing grade trypsin, chymotrypsin, endoproteinase Asp-N and Olu-C from Boehringer Mannheim. Iodoacetic acid was purchased from Sigma, dithiothreitol from Calbiochem. HPLC grade trifluoroscetic acid was obtained from Applied Biosystems, Inc. (Foster City, Calif.); HPLC-trade acetonitrile and water from Burdick & Jackson; 6N HCl from Pierce; and Vydac HPLC columns from the Nest Group (Southboro, Mass.). Automated sequencer and analyzer reagents were provided by the manufacturer. All other reagents were purchased from common commercial sources in the highest grade available.

Reduction and Alkylation of Inhibitory Factor

Inhibitory factor destined for proteolytic cleavage was reduced and S-carboxymethylated as described by Stone et al, *Techniques in Protein Chemistry* (Hugli, ed.) Academic Press, San Diego, pp. 377–391, (1989). 6.0 μg (300 pmol) aliquots of bovine inhibitory factor were dissolved in 50 μl 8M urea/0.4M $NH_4HCO_3$ and reduced with 5 μl of 45 mM dithiothreitol at 50° C. for 15 min. Cysteine residues were alkylated by reaction with 5 λ of 100 mM iodoacetic acid at room temperature for 15 min. Subsequent enzymic cleavage was carried out without further desalting or transfer as described below.

Proteolytic Cleavage of Inhibitory Factor

Trypsin, chymotrypsin digestions: The above alkylation mixture containing S-carboxymethylated bovine inhibitory factor was diluted fourfold without further processing (Stone et al, supra 1989) to a final buffer concentration of 2M urea/0.1M $NH_4HCO_3$. Enzyme was added to this solution to maintain a substrate to enzyme ratio of 25:1 (w/w), and the mixture was allowed to incubate at 37° C. for 20 hr. The resultant peptide mixture was frozen at −20° C. until a separation by reverse-phase HPLC was performed.

Narrow-Bore Reverse-Phase HPLC Separation of Peptides

Peptides were chromatographed on a Hewlett-Packard 1090 HPLC equipped with a 1040 diode array detector, using a Vydac 2.1 mm×150 mm C18 column. The gradient employed was a modification of that previously described by Stone et al, supra, (1989). Briefly, where buffer A was 0.06% trifluoroacetic acid/ $H_2O$ and buffer B was 0.055% trifluoroacetic acid/acetonitrile, a gradient of 5% B at 0 min, 33% B at 63 min, 60% B at 95 min, and 80% B at 105 min with a flow rate of 150 μl/min was used. Chromatographic data at 210 nm, 277 nm, 292 nm, and UV spectra from 209–321 nm of each peak were acquired. While monitoring absorbance at 210 nm, fractions were manually collected into 1.5 ml microfuge tubes and immediately stored without drying at −20° C. in preparation for peptide sequence analysis.

The inhibitory factor was unable to be analyzed and believed to have been refractory to those standard procedures; thus, alternative procedures were developed.

Analytical Step to Show that the Bovine Inhibitory Factor Can be Proteolytically Cleaved Since inhibitory factor could not be cleaved with either trypsin or chymotrypsin, a series of analytical tests were run with bovine inhibitory factor, using 5 micrograms per assay, to determine if the 18 kDa bovine inhibitory factor could be proteolytically cleaved.

The inhibitory factor was first solubilized in phosphate buffered saline (PBS, pH 7.0), heated to 95° C. for 5 min. to denature the polypeptide and then cooled to room temperature prior to the addition of the enzymes which were in 0.2M ammonium bicarbonate (pH 8.0). The two enzymes used were bovine pancreatic trypsin (TPCK-treated) (Sigma Chem. Co., catalog # T-8642), and endoproteinase Asp-N (Sigma Chem. Co., catalog # P-3303, suitable for sequencing and peptide mapping). Other suitfrom the group includinsen from the group including Olu-C and pronase, trypsin, chymotrypsin, B substilysin, serine proteases, thiolproteases, cathepsin D proteases, sulphydryl protease, metallo-proteases, trypsin like protease, estrase and carboxy proteases, non-specific proteases and other specific proteases.

Five micrograms of the inhibitory factor, in PBS, were incubated for 1 hour at 37° C., in a thermal cycler (reaction volume of 25 to 30 microliters), at an enzyme/substrate ratio of 1:10, 1:50 or 1:100; i.e., 0.5 microgram of enzyme, 0.1 microgram of enzyme, 0.05 microgram of enzyme. Controls were also run with the inhibitory factor incubated and handled in an identical manner, but without either the trypsin or endoproteinase Asp-N added. Reactions were terminated by raising the temperature to 70° C. in the thermal cycler.

The resulting reactants were analyzed by SDS-PAGE (Lakshmanarao et al, supra 1991) and silver-staining as described by Merril et al, Methods Enzymol. 104: 441–447 (1984). All three trypsin concentrations completely hydrolyzed the 18 kDa inhibitory factor and little, if any remaining substrate could be visualized on the gels. Both of the higher concentrations of endoproteinase Asp-N almost completely hydolyzed the 18 kDa substrate, while the lower concentration clearly was effective but some substrate (maybe one-third) remained as an 18 kDa band. In any event, the inhibitory factor clearly is sensitive to proteolytic hydrolysis. Using these new conditions following heat denaturation.

The resulting fragments are then separated and sequenced. For preparatory scale work the fragmentation of the purified 18 kDa bovine inhibitory factor (described in Example III), is carried out essentially as described above but with approximately 25 to 50 µg with an enzyme/protein ratio of at least 1:50. This provides adequate quantities of the fragments for separation of the fragments by HPLC and subsequent sequencing by routine methods.

Amino Acid Analysis of the 18 kDa Bovine Inhibitory Factor

Standard amino acid analysis was carried out on a sample of inhibitory factor. Based on the known mass of the inhibitory factor and the knowledge that it is a glycosylased molecule with less than 10% of the mass composed of carbohydrates, the amino acid composition was estimated. The total number of amino acids per bovine inhibitory factor molecule appears to be 153, and the identity of the amino acids is shown below.

Amino Acid Composition of the 18 kDa Bovine Inhibitory Factor

| Amino Acid(s)* | Number of Residues per Molecule |
|---|---|
| Asp/Asn (D&N) | 15 |
| Glu/Cln (E&Q) | 25 |
| Ser (S) | 17 |
| Gly (G) | 24 |
| His (H) | 3 |
| Arg (R) | 3 |
| Thr (T) | 8 |
| Ala (A) | 12 |
| Pro (P) | 11 |
| Tyr (Y) | 1 |
| Val (V) | 6 |
| Met (M) | 0 |
| Ilu (I) | 3 |
| Leu (L) | 6 |
| Phe (F) | 2 |
| Lys (K) | 13 |
| Total = | 149 |

*Both the three- and one-letter abbreviations for the amino acids are listed

This analysis is based on the most likely fit knowing that the bovine inhibitory factor is approximately 18 kDa had having carbohydrate residues that compose no more than 10% of the mass.

The DNA sequence encoding inhibitory factor can be obtained using routine procedures for synthesizing oligonucleotide probes using the amino acid sequence, and screening libraries. See Sambrook et al., *Molecular Cloning A Laboratory Manual*, 2d Edition, Cold Spring Harbor Laboratory Press, Chapter 11, 1989; Heller et al., Biotechniques 12, No. 1, p. 30–35 (1992); Itakura et al, Annual Rev. of Biochem, 53, 323–356 (1984); or Wood et al, PNAS, 82, 1585–1588 (1985).

Example V

Antibody Production

Rabbit polyclonal antibody against the native (nondenatured) form of the inhibitory factor was prepared by subcutaneous injection of New Zealand white rabbits with 200 µg of the 18 kDa bovine inhibitory factor purified as in Example 1 in an equal volume of Freund's complete adjuvant or mixed with Titermax™ adjuvant and as described by Lakshmanarao et al. Exptl. Cell Res. 195, 412–415, (1991). Alternatively, the autoimmune offspring of a male Balb/c/J mouse and a female Balb/AJ mouse are used. Further boosting once a month with antigen in complete Fruends adjacent has resulted in higher avidity antibody. In order to detect the reduced and denatured antigen by Western blot analysis antibody also was prepared against the reduced and denatured inhibitory factor. The 18 kDa inhibitory factor band, recovered from Laemmli, SDS-PAGE was excised, minced and passed through a syringe several times and blended with an equal volume of Freund's complete adjuvant. Rabbits were then immunized in the same manner as described above. Serum IgG, obtained with both the native and denatured forms of the bovine inhibitory factor was purified with a DEAE affigel blue column and by ammonium sulfate precipitation (Lakshmanarao et al., Exptl. Cell Res. 195, 412–415, 1991).

Example VI

Purification of the Parental Inhibitory Factor

Plasma membrane preparation and NaCl release—Plasma membranes were obtained from cell suspensions of bovine cerebral cortex tissue homogenized by 10 strokes in a Dounce homogenizer. The homogenate was centrifuged at 1,000×g for 15 min, and the supernatant fluid was collected and recentrifuged at 1,000×g for 15 min. The resulting supernatant fluid was centrifuged at 40,000×g for 60 min to pellet the plasma membranes, and the membrane-associated proteins were released by resuspending the pellet in 10 vol of a buffered 3M NaCl solution (3M NaCl, 0.1M phosphate buffer, pH 7.2, containing 1 µg/µl each of phosphoramidon, pepstatin A, leupeptin and aprotinin). The membrane suspension was mixed for 30 min at 4° C., centrifuged at 104,000×g for 60 min and the supernatant fluid was collected and dialyzed overnight at 4° C. The samples were first dialyzed against 1M NaCl, followed by three changes of double-distilled water and after dialysis protein determinations were carried out by the method of Bradford, Anal. Biochem. 72, 248–254 (1976).

Preparative isoelectric focusing—The NaCl-released membrane proteins were resuspended in 40 ml of double-distilled water, and electrofocused at 12 W for 4 h with 2% amphylines (pH 4–10, Pharmacia-LKB Biotechnology Inc., Gaithersburg, Md.) in a BioRad Rotofor apparatus (Bio-Rad, Richmond, Calif.). The resulting 20 (2 ml) fractions were dialyzed against three changes of dilute PBS and concentrated to dryness in a Savant Speedvac (Savant Instruments Inc., Hicksville, N.Y.).

Lectin affinity chromatography—The electrofocused samples were solubilized in working buffer (50 mM Tris-HCl, 10 mM $CaCl_2$, pH 8.0) and then added to a column (1 ml bed-volume) of *Limulus polyhemus* agglutinin (LPA) (EY Laboratories, San Mateo, Calif.) that previously was equilibrated with working buffer. The samples were incubated with constant mixing for 1 h at room temperature, and the column was then washed with working buffer until no eluting protein ($A_{280}$) could be detected. The bound proteins were eluted with elution buffer (50 mM Tris-HCl, 2 mM EDTA, pH 8.0), and both the bound and unbound fractions were extensively dialyzed at 4° C. against dilute PBS and lyophilized to dryness. Equal volume samples of the dialysis fluids were also lyophilized as controls for measurements of biological inhibitory activity.

Antibody affinity chromatography—IgG (1 mg) prepared to the native inhibitory factor was bound overnight at 4° C. to 1 ml of prewashed Affi-Gel HZ beads (Bio-Rad, Richmond, Calif.) following the protocol provided by the commercial supplier. The protein fraction that isoelectric focused at pI 5.1 (~1 mg protein) was added to the column, incubated overnight at 4° C. and the column was then washed with column buffer until no eluting protein ($A_{280}$) could be detected. 3M $MgCl_2$ (pH 7.1) was used to release the bound proteins, and the eluted protein fractions were collected, pooled, dialyzed overnight against dilute PBS at 4° C. and lyophilized to dryness.

Western analysis and immunoblots—Western analysis was carried out with a polyclonal antibody raised against the denatured bovine inhibitory factor essentially as described above. Immunoblots were carried out by transferring samples to nitrocellulose using a crossblot apparatus (Sebia, Paris, France), blots were then analyzed with antibody prepared to the native inhibitory factor and the relative antigenicity of various protein bands was determined by densitometric scanning (Lakshmanarao et al., Exptl. Cell Res. 195, 412–415, 1991).

Protein synthesis inhibition assay—At various stages of purification the ability of samples to inhibit protein synthesis was tested with Swiss 3T3 cells essentially as described by Sharifi et al., J. Neurochem. 46, 461–469, (1986).

Cell proliferation inhibition assay—Cell proliferation inhibition was measured with exponentially dividing cultures of Swiss 3T3 cells propagated in 48-well plates as described by Fattaey et al., J. Cell Physiol. 139, 269–274, (1989). The total medium volume of all cultures was 300 $\mu$l, and one set of control cultures received 40 $\mu$l of PBS while another received 40 $\mu$l of the lyophilized dialysis fluids that were solubilized in 1 ml of sterile double-distilled water. Experimental cultures received complete culture medium with 40 $\mu$l containing various concentrations of LPA bound or unbound protein solubilized in 1 ml of sterile double-distilled water. At the start of the experiment and after various periods of incubation with the additives cell numbers in each well were determined with a Coulter Counter, model ZM as described by Fattaey et al supra. (1989). Comparisons of cell proliferation were determined by the formula $[F_{exp}-A_{exp}]/[F_{cont}-A_{cont}] \times 100$ where A was the cell number (7.5×10) when the medium supplements were added, and F was the final cell number in the PBS (cont) and experimental (exp) wells at the end of the experiment.

As a preliminary assessment of the nature of the association of the parental inhibitory factor with the bovine cerebral cortex membranes, 50 mg protein aliquots of membrane preparations were incubated with either isotonic buffer, 3M NaCl or 3M urea at 4° C. for 30 min. and the membranes were then pelleted by centrifugation as described above. Immunoblot analysis of the membrane soluble extract and the pelleted membrane fractions, using polyclonal IgG raised to the native form of the inhibitory factor, revealed that the antigenic material was not released from the membranes when they were incubated in isotonic buffer. Incubation of membranes with 3M NaCl, however, efficiently released the majority of the antigenic component suggesting that the parental inhibitory factor was not an integral membrane component but rather a membrane-associated element. Treatment of membranes with 3.0M urea, another regent commonly used to release membrane-associated proteins, rendered both the soluble and the membrane fractions non-reactive to the polyclonal IgG against the native bovine inhibitory factor (FIG. 1). The loss of antigenicity of both the membrane and soluble fractions suggested that the incubation period with 3M urea denatured the antigenic material and rendered it nonreactive. Since the denatured form of the parental bovine inhibitory factor most likely would not be biologically active, further use of 3M urea to release the molecule from membranes was not pursued.

Since 3M NaCl proved to efficiently release virtually all of the antigenically-reactive material from cell membrane preparations, we were led to utilize this reagent as our initial step in the parental inhibitory factor purification scheme. In order to purify a greater quantity of the parental inhibitory factor, 500 mg protein of the membrane preparation was subjected to 3M NaCl treatment which yielded 85 mg of protein (17% of the total membrane protein), and a six-fold purification of the parental inhibitory factor (Table 1).

TABLE 1

| Purification of the 66 kDa Inhibitory Factor | | | | | |
|---|---|---|---|---|---|
| | Initial Protein | Recovered Protein | | Fold Purification | | Number of |
| Preparation | (mg) | (mg) | (%) | Step | Total | Experiments |
| Membranes | | 500.0 | 100.0 | — | — | — |
| 3M NaCl Released | 500 | 85.0 | 17.0 | 6 | 6 | 10 |
| Preparative IEF | 85 | 4.0 | 0.8 | 21 | 126 | 8 |
| LPA Affinity Chromatography | 1 | 0.048 | 0.05 | 20 | 2,520 | 3 |

Figure 2:
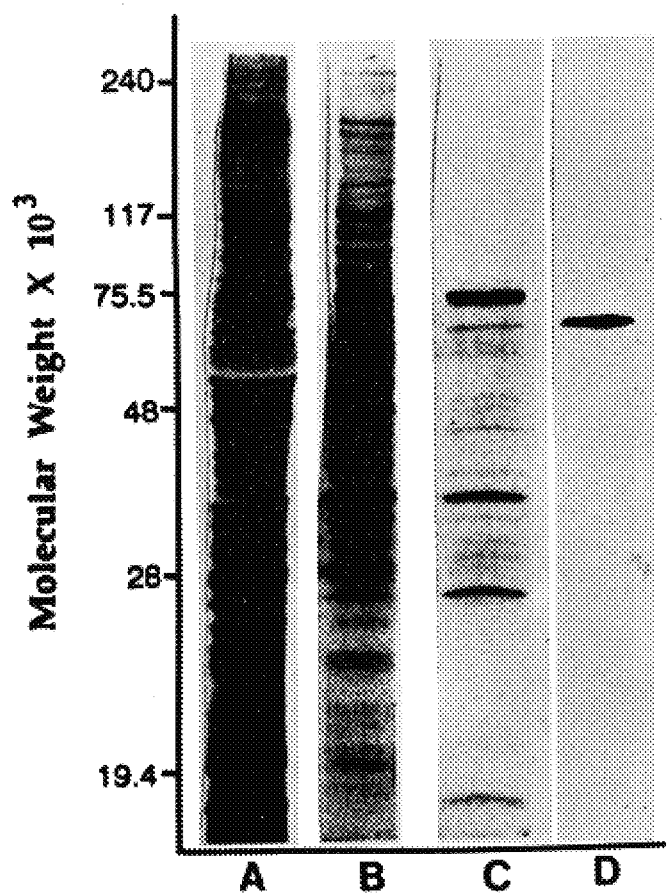
FIG. 2 shows an SDS-PAGE analysis of bovine brain cerebral cortex cell membrane proteins during purification. Samples were separated by SDS-PAGE under reducing conditions, and the gels were then silver stained. Original membrane preparation (100 $\mu g$ protein, lane A), 3M NaCl released membrane proteins (50 $\mu g$ protein, lane B), preparative isoelectric focused pI 5.1 purified proteins (10 $\mu g$ protein, lane C) and LPA affinity chromatography purified sample (5 $\mu g$ protein, lane D).

SDS-PAGE analysis of this initial extract revealed numerous protein bands indicating the necessity for further purification (FIG. 2, lane B).

Figure 3:
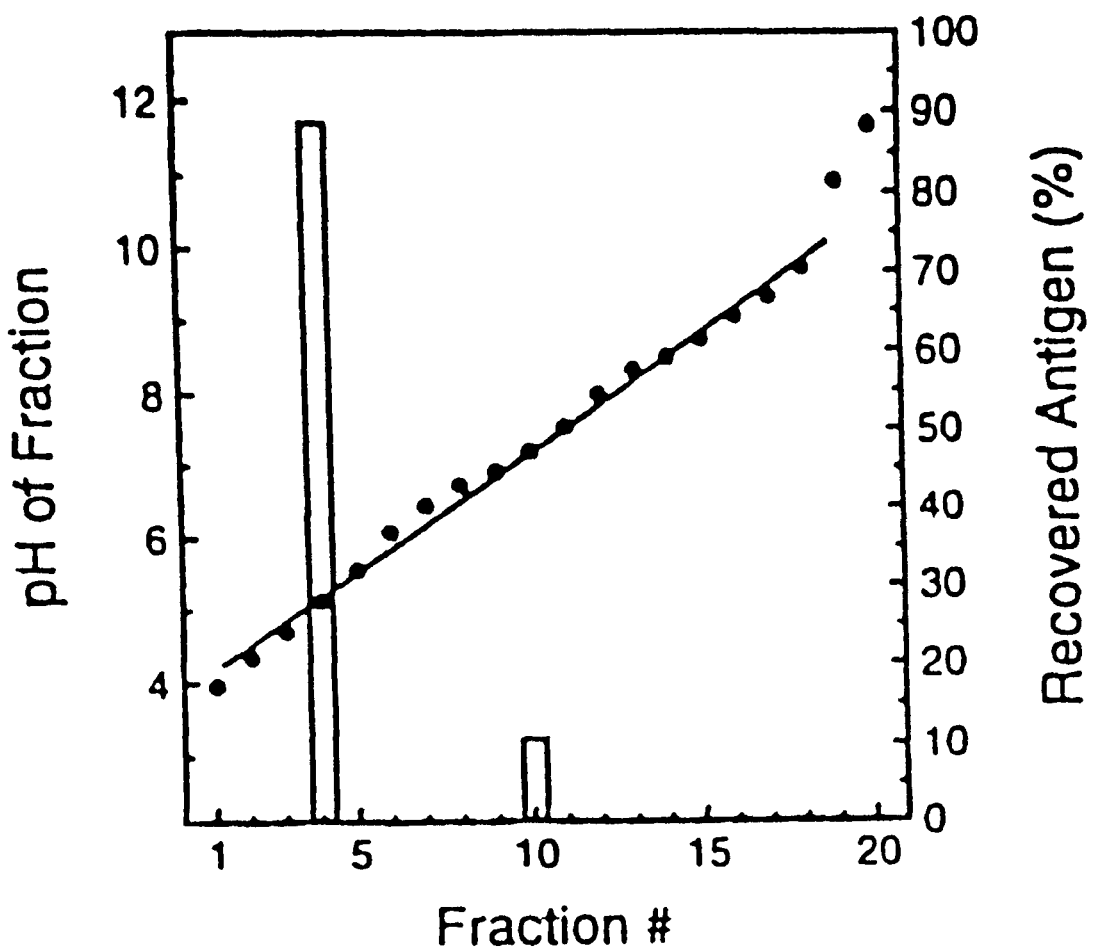
FIG. 3 shows preparative isoelectric focusing analysis of 3M NaCl released proteins from membranes of bovine brain cerebral cortex cells. 1 mg membrane protein, released by 3M NaCl, was isoelectrofocused as described in the Materials and Methods, and the pH of the twenty 2 ml fractions was measured. 50 $\mu g$ protein from each fraction was analyzed by immunoblot using polyclonal antibody against the native bovine inhibitory factor. The relative amount of antigen in each fraction was quantified by densitometer scanning.

The NaCl-released membrane proteins were next subjected to preparative isoelectric focusing utilizing a BioRad Rotofor as described in the Materials and Methods. 85 mg of the NaCl-released proteins were introduced to the Rotofor unit, the material was focused for 4 h and 20 fractions (2 ml) were collected across a pH gradient from 4.0 to 12.0. The proteins were relatively equally distributed across the gradient with each fraction having somewhere between 3.5 to 4.0 mg of protein. Immunoblot analysis of each fraction revealed that the antigenically-reactive material primarily was associated with two fractions: a major reactive peak was found to be focused at a pI of 5.1 (fraction number 4); and, a minor reactive peak was focused at a pI of 7.2 (fraction number 10) (FIG. 3). Approximately 90% of the reactive antigen was focused at pH 5.1, and the amount of protein recovered constituted 0.8% of the original membrane protein. No antigenically reactive materials could be found by immunoblot analysis in the remaining 18 fractions (FIG. 3). At this stage of purification the parental inhibitory factor was purified approximately 123-fold (Table 1). However, there still was a heterogenous array of protein bands when the isoelectric focused fraction at pH 5.1 was analyzed by SDS-PAGE and developed by silver staining (FIG. 2, lane C). Although there were three distinct major bands, an additional 12 minor bands were detected at this stage of the purification.

Because previous information had shown that the inhibitory factor contained sialic acid residues (Sharifi et al., J. Neurochem. 46, 461–469, 1986), we took advantage of *Limulus polyhemus* agglutinin (LPA) lectin affinity chromatography to further purify the parental inhibitory factor. 1 mg protein of the immunoreactive pI 5.1 fraction, obtained by preparative isoelectric focusing, was loaded on a LPA column as described above, the column was extensively washed with working buffer and the bound material was then released (48 μg protein) with an elution buffer containing 2 mM EDTA. SDS PAGE analysis of the LPA bound and released protein preparation provided a single band at approximately 66 kDa (FIG. 2, lane D). A visual comparison of the LPA and Rotofor purified fractions clearly showed that the 66 kDa band was a relatively minor component of the isoelectric focused material. Since the SDS-PAGE gel was run with the LPA fractioned protein, reduced just prior to gel analysis, and no other bands were evident by silver staining, we concluded that the parental inhibitory factor most likely was a single polypeptide without subunit structure. At this stage of the purification the parental inhibitory factor appeared homogeneous, and enriched 2,520-fold over the original membrane protein (Table 1).

Affinity columns with immobilized polyclonal IgG, raised to the native inhibitory factor, also were used in the purification protocol. A 66 kDa molecule was bound and eluted from the column, and the small amount of recovered protein (approximately 1 to 2 μg) was insufficient to test biological inhibitory activity. Within the resolution of SDS-PAGE gels stained with silver stain, the IgG affinity purified parental inhibitory factor appeared similar to that obtained by LPA affinity chromatography.

To provide assurance that the 66 kDa protein, obtained by LPA affinity chromatography was antigenically related to the inhibitory factor, dot blot analyses were conducted with polyclonal IgG raised against the native inhibitory factor. 200 ng protein of both the LPA bound and eluted, and the LPA unbound fractions were blotted and probed with the anti-inhibitory factor IgG. The bound and eluted fraction was strongly antigenic while the unbound material showed only slight reactivity that most likely reflected a slight overloading of the affinity column. Western analyses, carried out with the IgG raised to the denatured inhibitory factor, were consistent with the dot-blot analyses and showed that only a 66 kDa band of LPA bound and eluted fraction reacted with the IgG, while the proteins in the unbound fraction essentially was nonreactive.

Both the purified 66 kDa membrane protein and the LPA unbound protein fraction were tested for biological inhibitory activity with exponentially dividing mouse Swiss 3T3 fibroblast cells. The lyophilized 66 kDa protein was resuspended in 1 ml of distilled water, and 40 μl containing 1, 5 or 10 μg of protein were added to culture medium to provide a total volume of 300 μl, resulting in final concentrations of the parental inhibitory factor of $5 \times 10^{-8}$M, $2.5 \times 10^{-7}$M and $5 \times 10^{-7}$M, respectively. The LPA unbound proteins were added at the same concentrations, and other sets of cultures received 40 μl of the dialysis fluids, previously lyophilized and resuspended in 1 ml of distilled water. The addition of the 66 kDa parental inhibitory factor clearly showed a marked inhibition of 3T3 cell division when compared to cultures that received the dialysis fluid or PBS (Table 1). The measured inhibition appeared at least semi-quantitative since the cultures receiving 10 μg ($5 \times 10^{-7}$M) of protein attained only 7% of the growth compared to the control and dialysis fluid-treated cultures, while the cultures receiving 5 μg ($2.5 \times 10^{-7}$M) and 1 μg ($5 \times 10^{-8}$M), attained 26% and 53%, respectively. In contrast, the cultures receiving the LPA unbound protein continued proliferating as those that received reconstituted dialysis fluid (Table 2).

TABLE 2

Inhibition of Cell Division by the 66 kDa Inhibitory Factor

| Additions to Culture Medium (in 40 μl) | Protein Added (μg) | Final Cell Number* ($\times 10^4$) | Growth Compared to Control** (%) |
|---|---|---|---|
| PBS (control) | — | 2.9 | 100 |
| Dialysis Fluid | — | 2.9 | 100 |
| 66 kDa Protein | 1 | 1.9 | 53 |
| 66 kDa Protein | 5 | 1.3 | 26 |
| 66 kDa Protein | 10 | 0.9 | 7 |
| PBS (control) | — | 2.5 | 100 |
| Dialysis Fluid | — | 2.8 | 117 |
| LPA-Unbound Protein | 1 | 2.5 | 100 |
| LPA-Unbound Protein | 5 | 2.8 | 117 |
| LPA-Unbound Protein | 10 | 2.4 | 94 |

*Each data point represents the mean of duplicate cultures and three independent measurements of cell number in each well.
**Additions were made when the total cell number per culture was $7.5 \times 10^3$, and cell proliferation was compared to those cultures receiving 40 μl of PBS Example VII Cloning of the Genes for Mouse, Bovine and Human Inhibitory Factor Immunoscreening of cDNA libraries with the polyclonal antibody prepared to the denatured inhibitory factor was carried out with commercially available cCNA libraries prepared from bovine cerebral cortex, human fetal brain and mouse kidney.

The preparation of the lambda bacteriophages, the immunological screening and identification of positive clones were essentially carried out by the procedures described in *Molecular Cloning: A Laboratory Manual* (J. Sambrook, E. F. Frisch and T. Manlatis, 2nd Edition, Cold Spring Harbor Laboratory press, 1989).

Preparation of the Host Bacteria (modified from Part 1 of the *Molecular Cloning: A Laboratory Manual* cited above).

50 ml of sterile rich medium (LB) supplemented with 0.2% maltose and 10 mM magnesium sulfate was placed in a sterile 250-ml flask and inoculated with a single bacterial colony. The culture was grown overnight at 37° C. with moderate agitation (250 cycles/minute in a rotary shaker). When XL1-Blue cells were to be used as the host as in the case of the HFB and BCC Libraries (see below) 5 micrograms of tetracycline was also added to the medium.

The cells were then centrifuged at 4000×g for 10 minutes at room temperature and resuspended in 5 ml to 10 ml of LB medium supplemented as described above.

Immunological Screening of Expression Libraries (from Part 2 of the *Molecular Cloning: A Laboratory Manual* cited above).

Screening Expression Libraries Constructed In Bacteriophage λ Vectors

Using a single colony of the appropriate strain of *E. coli* as inoculum, prepare a plating culture as described in Chapter 2 of *Molecular Cloning: A Laboratory Manual.*

*E. coli* strain Y1090hsdR, which is commonly used as the host for immunological screening of expression libraries constructed in λgt11 as was the case for the MK library (see below), carries a plasmid (pMC9) that codes for the lac repressor and prevents synthesis of potentially toxic fusion proteins from the β-galactosidase promoter. This plasmid also carries a selectable marker (amp$^r$). To ensure against loss of the plasmid, *E. coli* strain Y1090hsdR was grown in media containing 50 μg/ml ampicillin.

*E. coli* strains BB4 and XL1-Blue, which were used for immunological screening of libraries constructed in λZAP, carry a lacI$^q$ gene and a tet$^r$ marker on an F' factor. These strains were therefore grown in media containing 12.5 μg/ml tetracycline.

Twenty plates were typically used. A set of sterile tubes (13 mm×100 mm) were arranged in a rack; a fresh tube was used for each plate infected. In each tube, 0.1 ml of the plating bacteria was mixed with 0.1 ml of sodium magnesium media (manniatis, supra) containing 3×10$^4$ pfu (90-mm plates) or 10$^5$ pfu (150 mm plates) of the bacteriophage λ expression library. The infected bacteria was incubated for 20 minutes at 37° C.

To each tube was added 4.0 ml (90-mm plate) or 7.5 ml (150-mm plate) of molten top agarose, and the mixture was immediately poured onto an LB agar plate. The infected plates were incubated for 3.5 hours at 42° C.

Nitrocellulose filters were numbered. The filters were handled with gloved hands. The filters were soaked in a solution of isopropylthio-β-n-galactoside (IPTG) (10 mM in distilled water) for a few minutes. One set of plates were done without IPTG—treated nitrocellulose as a control. Using blunt-ended forceps (e.g., Millipore forceps), the filters were removed from the solution, and allowed to dry at room temperature on a pad of Kimwipes.

The plates were removed from the incubator, and the agar quickly overlayed with the IPTG-impregnated nitrocellulose filters.

The lids were left off the plates and the incubation continued for a further 20 minutes at 37° C.

The plates were moved in small batches to room temperature. Each filter was marked in at least three asymmetric locations by stabbing through it and into the agar underneath with an 18-guage needle attached to a syringe containing waterproof black ink.

Using blunt-ended forceps, the filters were peeled off the plates and immediately immersed in a large volume of TNT. Any small remnants of agarose was rinsed away by gently agitating the filters in the buffer. The TNT was agitated to prevent the filters from sticking to one another.

TNT
  10 mM Tris Cl (pH 8.0)
  150 mM NaCl
  0.05% Tween 20

The plates were wrapped in Saran Wrap, and stored at 4° C. until the results of the immunological screening were available.

When all of the filters are removed and rinsed, they are transferred one at a time to a fresh batch of TNT. When all of the filters have been transferred, the buffer is agitated gently for a further 30 minutes at room temperature.

Using blunt-ended forceps, the filters were transferred individually to glass trays or petri dishes containing blocking buffer (7.5 ml for each 82-mm filter; 15 ml for each 138-mm filter). When all of the filters had been submerged, the buffer was agitated slowly on a rotary platform for 30 minutes at room temperature.

Blocking Buffer

2% nonfat dry milk in TNT

The blocking buffer was stored at 4° C. and reused several times. Sodium azide was added to a final concentration of 0.05% to inhibit the growth of microorganisms.

Using blunt-ended forceps, the filters were transferred to fresh glass trays or petri dishes containing the primary antibody diluted in blocking buffer (7.5 ml for each 82-mm filter; 15 ml for each 138-mm filter). The highest dilution of antibody was used that gives acceptable background yet still allows detection of 50–100 pg of denatured antigen. When all of the filters had been submerged, the solutions were agitated gently on a rotary platform overnight at room temperature.

The antibody solution was stored at 4° C. and reused several times. Sodium azide was added to a final concentration of 0.05% to inhibit the growth of microorganisms.

The filters were washed for 10 minutes in each of the buffers below in the order given. The filters were transferred individually from one buffer to the next. 7.5 ml of each buffer was used for each 82-mm filter and 15 ml for each 138-mm filter.

TNT+2% nonfat dry milk
  TNT+2% nonfat dry milk+0.1% Nonidet P-40
  TNT+2% nonfat dry milk.

The antigen-antibody complexes were detected with the radiochemical reagents.

Approximately 1 μCi of $^{125}$I-labeled protein A (the preferred reagent) or anti-immunoglobulin were used per filter. Radiolabeled protein A is available from commercial sources (sp. act. 30 mCi/mg). Radioiodinated second antibody is prepared according to well known techniques. Radiolabeled ligands were diluted in blocking buffer (7.5 ml for each 82-mm filter; 15 ml for each 138-mm filter). The filters were incubated 2 hrs. at room temperature, and then washed several times in TNT before autoradiographs were established.

The locations of positive plaques were identified.

a. A sheet of Saran Wrap was layed over t he filters.

b. On the surface of the Saran Wrap, the locations of the holes in the filters and the locations of antigen-positive clones were marked with different colored waterproof markers. The Saran Wrap was labeled to identify the plates from which the filters were derived.

c. The shee t of Saran Wrap was placed on a light box, and the plates were aligned containing the original bacteriophage λ plaques on top of it.

d. The area containing the positive plaque is identified, and a plug of agar from this area is removed using the large end of a pasteur pipette. The plug was transferred to 1 ml of SM containing 2 drops of chloroform.

e. The sheet of Saran Wrap, which provides a permanent record of the locations of the positive plaques is retained.

The bacteriophage particles were allowed to elute from the agar plug for several hours at 4° C. The titer of the bacteriophages in the eluate was determined, and then replated so as to obtain approximately 3000 plaques per 90-mm plate. The plaques were rescreened as described above, and the process of screening and plating was repeated until a homogeneous population of immunopositive recombinant bacteriophages was obtained. The clonal isolates were subcloned at least three times to provide a homogeneous positive population, and each time the plaques were tested with the polyclonal antibody probe to provide assurance of continued antigen product expression and the homogeneity of the final isolate.

The results were as follows:

Bovine Cerebral Cortex Library (BCC), lambda ZAPII phage/XL-1-Blue *E. coli* host, 2,000,000 plaques screened, five positive clones; the five positive clones were pooled and labelled "B" and deported at the ATCC on Apr. 27, 1992.

Human Fetal Brain Library (HFB), lambda ZAPII phage/ XL-1-Blue *E. coli* host, 4,000,000 plaques screened, three positive clones; the three positive clones were pooled and labelled "M" and deposited at the ATCC on Apr. 27, 1992, and, Mouse Kidney Library (MK), lambda g1ll phage/Y1090 *E. coil* host, 5,000,000 plaques screened, two positive clones; the two positive clones were pooled and labelled "H" and deposited at the ATCC on Apr. 27, 1992.

Lambda DNA Isolation

Three separate protocols were used in order to isolate lambda DNA but only one way led to successfully isolating sufficient DNA for sequencing. All three methods used the same general protocol to grow the host and phage.

Two 20-ml starter cultures of bacteria were grown overnight in LB medium supplemented with maltose and magnesium sulfate as described above. A lambda virus p reparation with a titer of $10^{10}$ plaque forming units per ml was mixed with 200 microliters of the host cell starter culture, and the preparation was incubated at 37° C. for 15 to 30 minutes. The preparation was then added to the 40 ml host culture and incubated at 37° C., with constant mixing, until lysis occurred (7 to 8 hours).

The three methods used for isolation of DNA were:

1) Promega Technical Bulletin No. 142, "Purification of Lamda DNA with Magic™Lamda Preps DNA Purification System", p. 3, "Liquid Culture Method," (steps 1 through 5); p. 4, "Removal of Lambda Phage Coat," (all steps); page 5 ignore; and, p. 6, "Lambda DNA Purification Without a Vacuum Maniford," (all steps). Using this technique, only 2 to 4 micrograms of lambda DNA were recovered.

2) Pharmacia P-L Biochemicals Bulletin, Sephaglas™ PhagePrep Kit (1991), pp. 9–12. Using this technique, only 2 to 4 micrograms of lambda DNA were recovered.

3) Modified techniques for isolation of lambda DNA.

After host cell lysis, 200 microliters of pure chloroform was added and the preparations were shaken at 37° C. for 5 minutes. The lysates were centrifuged at 1000×g for 15 minutes to pellet debris. The supernatant fluids were centrifuged at 40,000×g at 4° C. for 1.5 hours to pellet the bacteriophage particles. The supernatant fluids were discarded, the phage pellets were drained and resuspended in a total of 300 microliters of 50 mM Tris-HCl (pH 7.5). The preparations were treated with DNase and RNase (1 microgram per m/l each) for 30 minutes at 37° C. The DNA was then extracted with 1 volume of TE buffer (10 mM Tris-HCl and 1 mM EDTA, pH 7.4) saturated with phenol plus chloroform and isoamylalcohol (50:48:2). The tubes were rocked gently for 1 minute, then centrifuged at 12,000×g at 4° C. for 5 minutes, and the initial extrarction was repeated.

The aqueous phase was then removed and extracted once with chloroform/isoamylalcohol (24:1) with gentle rocking for 1 minute. The mixture was centrifuged at 12,000×g at 4° C. for 5 minutes and the aqueous phase removed. An equal volume of isopropanol was added, the tubes rocked gently, and the mixture was left at −70° C. for at least 20 minutes. The mixture was again centrifuged at 12,000×g at 4° C. for 10 minutes and the supernatant fluid was removed. The pellet was rinsed by adding 1 ml of 70% ethanol, followed by immediate centrifugation at 12,000×g at 4° C. for 10 minutes. The resulting pellet was air-dried and resuspended in 50 microliters of 50 mM Tris-HCl (pH 7.5).

This method provided 35 micrograms of lambda DNA.

The preparation of this example was an isolate with a 1.3 kilobase pair insert, obtained from the human fetal brain cDNA library.

The DNA inserts removed by restriction enzymes or pcr were then subcloned into the vector p-Flag system, available commercially from International Biotechnologies, Inc. (New Haven, Conn.), in either XL1-Blue or JM101 *E. coli* hosts. Each subclone was tested for inducibility, fusion proteins isolated from the microbial periplasm and identified by We stern analysis. The purified fusion proteins are tested for biological inhibitory activity by assays described above.

Example VIII

Effects of Inhibitory Factor on the Post-Translational Regulation of the Retinoblastoma Protein Inhibitory factor mediated cell cycle arrest of both human diploid fibroblasts (HSBP) and mouse fibroblasts (Swiss 3T3) results in the maintenance of the RB protein in the hypophosphorylated state, consistent with a late G1 arrest site. Although their normal nontransformed counterparts are sensitive to cell cycle arrest mediated by inhibitory factor, cell lines lacking a functional RB protein, through either genetic mutation or DNA tumor virus oncoprotein interaction, are refractory.

Inhibitory factor purification. The sialoglycopeptide inhibitory factor inhibitor was released from intact bovine cerebral cortex cells by mild proteolysis and purified to apparent homogeneity as described above. Briefly, bovine cerebral cortex cells were treated with dilute protease, the released molecules precipitated with ethanol, the precipitates were extracted with chloroform/methanol (2:2), and inhibitory factor was purified by DEAE ion-exchange chromatography, lectin affinity chromatography and HPLC with a TSK-3000 size exclusion column. The samples were then dialyzed against distilled water, lyophilized and resuspended in phosphate buffered saline (PBS; 145 mM NaCl, 5 mM potassium phosphate, pH 7.2). Protein determinations were carried out by the method of Bradford, et al, Anal. Biochem. 72: 248–254 (1976) using bovine serum albumin as a protein standard, and the purified inhibitory factor preparations were stored at −70° C.

Cell culture. Cultures were grown as monolayers in a humidified incubator with a 5% $CO_2$/95% air atmosphere Fattaey, et al, J. Cell. Physiol. 139: 269–274 (1989). Mouse Swiss 3T3 cells, from the American Type Culture Collection, and the SV40 transformed 3T3 cell lines (SVT2 and F5B), were grown in Dulbecco's modified Eagle's medium (DMEM) (GIBCO/BRL, Grand Island, N.Y.) with 10% calf serum. Human diploid foreskin fibroblasts (HSBP), human osteosarcoma cells (U2OS and SAOS-2), human bladder carcinoma cells (J82), human prostate carcinoma cells (DU145), and adenovirus transformed human epithelial cells (293) and grown in DMEM with 10% fetal calf serum. Human fibroblast keratinocytes (HFK), and HFK cells transformed with papillomaviruses (28-NCO and 1321) Pietenpol, et al, Cell 61: 777–785 (1990); Romanczuk, et al, J. Virol. 65: 2739–2744 (1991) and grown in KGM media with growth factors (Clonetics, San Diego, Calif.).

Protein synthesis inhibition say. Protein synthesis inhibition was tested essentially as described by Sharifi et al, J. Neurochem. 46: 461–469 (1986). Various concentrations of the purified inhibitory factor were added to $5 \times 10^5$ cells in 100 µl of methionine-free minimal Eagle's medium (MEM/HEPES). The cells were preincubated with the inhibitor for 30 min at 37° C. to allow inhibitory factor to bind to the cell surface receptor, and then 2.0 µCi of [$^{35}$S]methionine, in 10 µl of methionine-free MEM/HEPES were added, and the cells were incubated for an additional 15 min. The cell proteins were precipitated with trichloroacetic acid (TCA), the precipitates were washed several times with 5% TCA, and the amount of radioactivity incorporated into acid-insoluble protein was measured in a liquid scintillation system Sharifi et al, J. Neurochem. 46: 461–469 (1986).

Cell proliferation assay. Cells were plated in 48-well culture plates (Costar, Cambridge, Mass.) and allowed to attached for at least 4 h. Then ~$6-9 \times 10^{-8}$M inhibitory factor, diluted in the appropriate culture medium, or medium alone, was added and the cell number determined at various times with a Coulter counter, model ZM Edson, et al, Life Sci. 48: 1813–1820 (1991) and Fattaey, et al, J. Cell. Physiol. 139: 269–274 (1989).

RB protein immunoprecipitation and SDS-PAGE. Cell cultures, incubated with and without inhibitory factor for 24 h, were radiolabelled for 3.5 h with 300 µCi/ml of [$^{35}$S] methionine (TRANS$^{35}$SLABEL, ICN, Irvine, Calif.) in methionine-free DMEM, and immunoprecipitated from cell lysates for 12 h as described by Harlow and Lane Harlow, et al, Antibodies: a laborarory manual, Cold Spring Harbor Press, New York (1988), using monoclonal anti-human IgG$_1$(PMG3-245, Pharminigen, San Diego, Calif.). Due to the lower reactivity between the mouse RB product and the PMG3-245 antibody, Swiss 3T3 lysates were incubated with the antibody for 24 h. The immunoprecipitates were boiled for 5 min in sample buffer Laemmli, V. K., Nature 227: 680–685 (1970) and separated on a 7.5% SDS-PAGE at 15 mA for ~3 h (samples were equalized with regard to the amount of radiolabelled protein loaded). After electrophoresis the proteins were electroblotted to a PVDF membrane (Millipore, Bedford, Mass.), prepared for fluorography (EN$^3$HANCE spray, NEN/DuPont, Willimington, Del.) and exposed to X-ray film for 24 h at −70° C.

Inhibitory factor binding assay. Inhibitory factor was radioiodinated, and the binding studies were carried out as described by Bascom et al, J. Cell. Physiol. 128: 202–208 (1986). Briefly, radioiodination was by the chloramine T method (Sigma Chem. CO., St. Louis, Mo.) that resulted in a biologically active inhibitory factor with a specific radio-activity of ~$1 \times 10^4$ cpm/ng protein. Cultures were grown in 24-well plates and various concentrations of the $^{125}$I-labelled inhibitory factor (in 300 µl of culture medium), with or without a 30-fold excess of nonradioactive inhibitory factor to measure nonspecific binding, were added to duplicate subconfluent cell cultures (~$1.5 \times 10^5$ cells/well). The cells were incubated with the radiolabelled inhibitor preparations at 37° C. for 30 min and then quickly washed three times with PBS. The cells were then lysed by the addition of 300 µl of distilled water containing 100 µl of 1M NaOH. The samples were collected and the bound radiolabelled inhibitory factor was determined with a gamma counter Bascom et al, J. Cell. Physiol. 128: 202–208 (1986).

Figure 4:
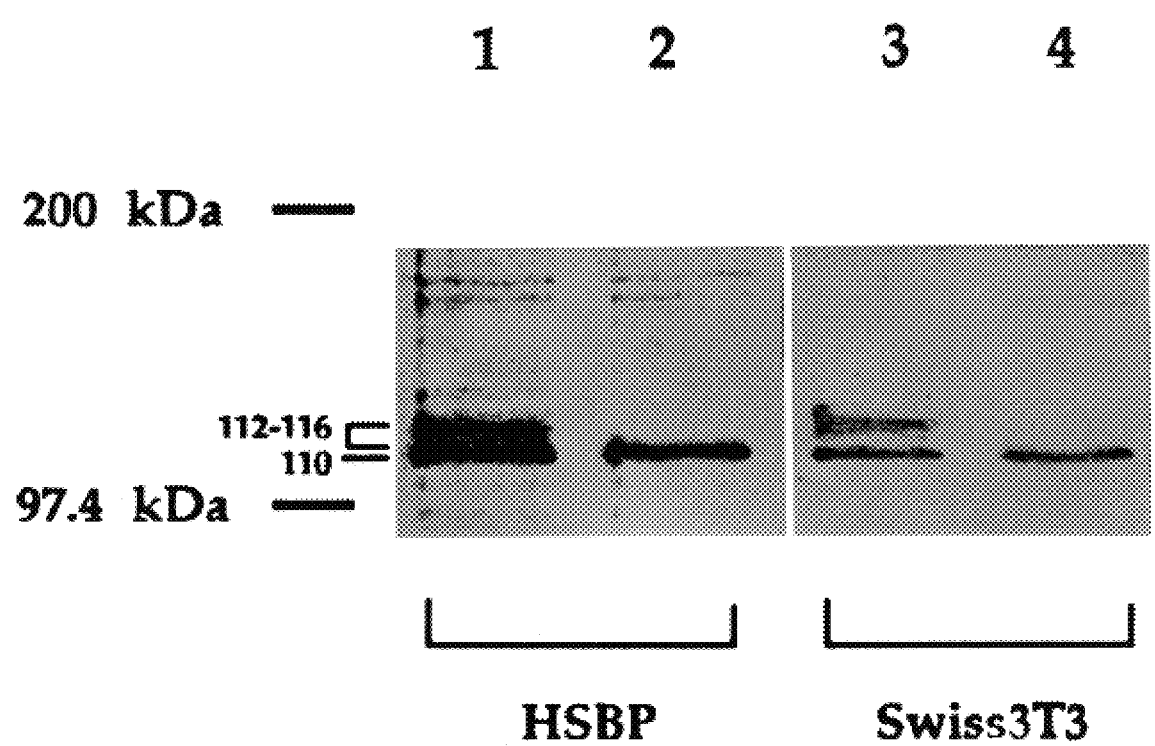
FIG. 4 shows RB protein immunoprecipitation of inhibitory factor arrested HSBP and Swiss 3T3 fibroblasts. Sparse HSBP and Swiss 3T3 cultures were treated for 24 hours with either, ~$6\times10^{-8}$M inhibitory factor in DMEM with 10% newborn calf serum, or DMEM alone as a control. The cells were then radiolabelled for 3½ hours with [$^{35}$S]methionine, immunoprecipitated with monoclonal mouse anti-human RB IgG$_1$, and the proteins separated by SDS-PAGE as described in Example VIII. Lane 1, control logarithmically growing HSBP cells; Lane 2, inhibitory factor arrested HSBP cells; Lane 3, control logarithmically growing Swiss 3T3 cells; and, Lane 4, inhibitory factor arrested Swiss 3T3 cells.

Exponentially growing human diploid fibroblasts (HSBP) and Swiss 3T3 cells were used to study the potential effect of inhibitory factor mediated cell cycle arrest on the phosphorylation states of the RB gene product. The cultures were incubated with or without inhibitory factor for 24 h, radiolabelled for 3.5 h with [$^{35}$S]methionine, and the RB protein was immunoprecipitated with the monoclonal anti-human RB IgG as described above. Both exponentially growing cell cultures exhibited newly synthesized RB protein in both the hypo- and hyperphosphorylated states (FIG. 4, lanes 1 & 3), while cells arrested by the inhibitory factor inhibitor contained only RB protein in the hypophosphorylated state (FIG. 4, lanes 2 & 4). These observations were consistent with the proposed G1 regulatory state of the RB protein and the site of cell cycle arrest mediated by the inhibitory factor inhibitor.

Figure 5:
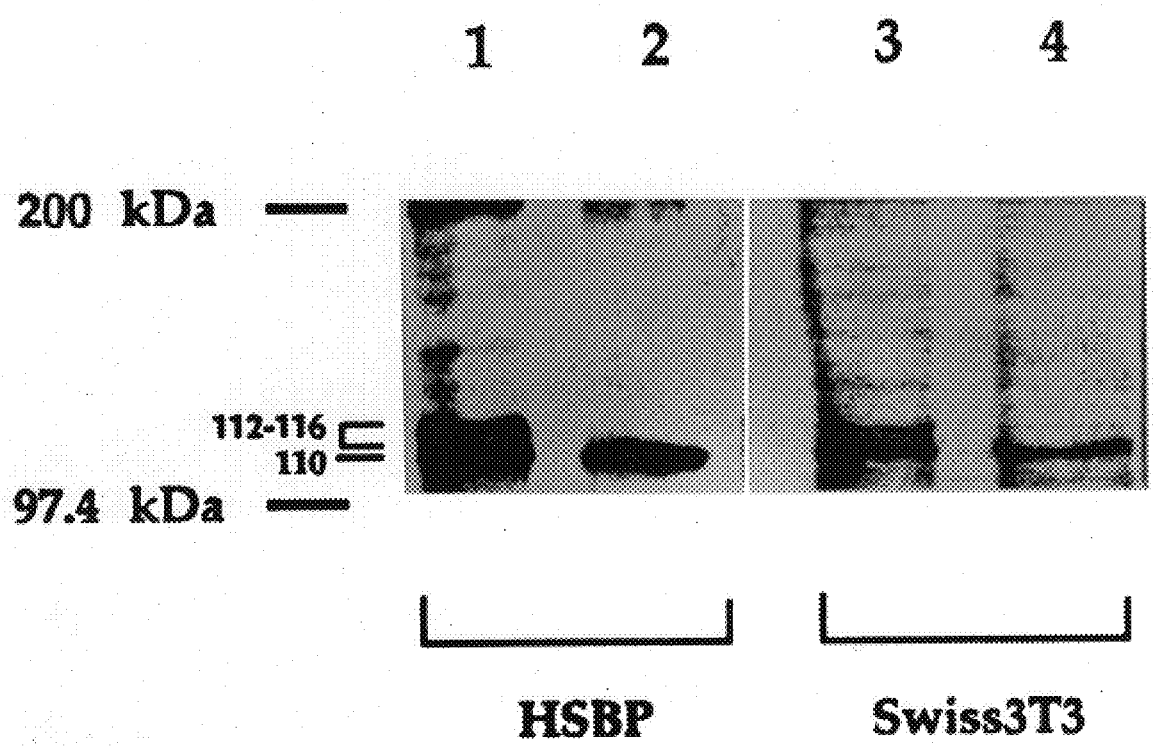
FIG. 5 shows RB protein immunoprecipitation of density-dependent quiescent HSBP and Swiss 3T3 fibroblasts. HSBP and Swiss 3T3 cells were plated and allowed to grow to confluence as described in Example VIII. After reaching confluency the cultures were incubated an additional 24 hours, and the cells were then radiolabelled and immunoprecipitated. Another set of HSBP and Swiss 3T3 cultures were plated on the same day at ~⅓ the density. These cells were treated in the same fashion as the first set however, at the time of immunoprecipitation were subconfluent. Lane 1, subconfluent HSBP cultures; Lane 2, confluent HSBP cultures; Lane 3, subconfluent Swiss 3T3 cultures; and, Lane 4, confluent Swiss 3T3 cultures.

To further examine the potential role of posttranslational modification of the RB product in the biological inhibitory action of inhibitory factor, both HSBP and Swiss 3T3 cells were plated and allowed to grow to confluence, and when the cultures reached confluence they were incubated for an additional 24 h to ensure that the majority of the cells were density-dependent arrested. A second set of cultures were plated at the same time at ~⅓ the density, and at the time of immunoprecipitation these cultures remained subconfluent. The results clearly showed that both HSBP an d 3T3 density-dependent growth arrested cultures solely displayed the RB$^{unphos}$ protein (FIG. 5, lanes 2 & 4). Exponentially dividing HSBP and 3T3 cells, however, again expressed the expected hyper- and hypophosphorylated forms of the RB product (FIG. 5, lanes 1 & 3). The results from these experiments indicated that cell cycle arrest, mediated by inhibitory factor, was consistent with a block at or near the G1 arrest site since the state of phosphorylation of the RB protein, under inhibitory factor mediated cell cycle arrest and density-dependent arrest, was indistinguishable.

These observations, however, did not necessarily establish a direct relationship between the RB protein and signal transduction events associated with the inhibitory factor inhibitor. If the maintenance of the RB protein in the RB$^{unphos}$ state is necessary for inhibitory factor mediated inhibition, cell lines either lacking a functional RB product or having the RB protein sequestered by a viral oncoprotein lead to an insensitivity to the cell cycle regulatory activity of the sialoglycopeptide.

Figure 6A:
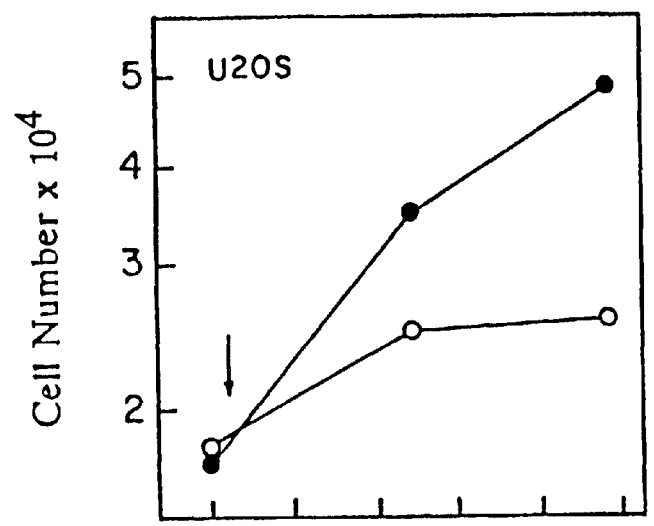
FIG. 6 shows inhibitory factor cell proliferation inhibition assays carried out on the human osteosarcoma U2OS (RB$^+$) and SAOS-2 (RB$^-$) cell lines. Osteosarcoma cells grown in DMEM and 10% fetal calf serum, and either $9\times10^{-8}$M inhibitory factor (○) or an equal volume of PBS (●) was added at the time indicated by the arrows. Data are plotted as the average of duplicate wells.
Figure 6B:
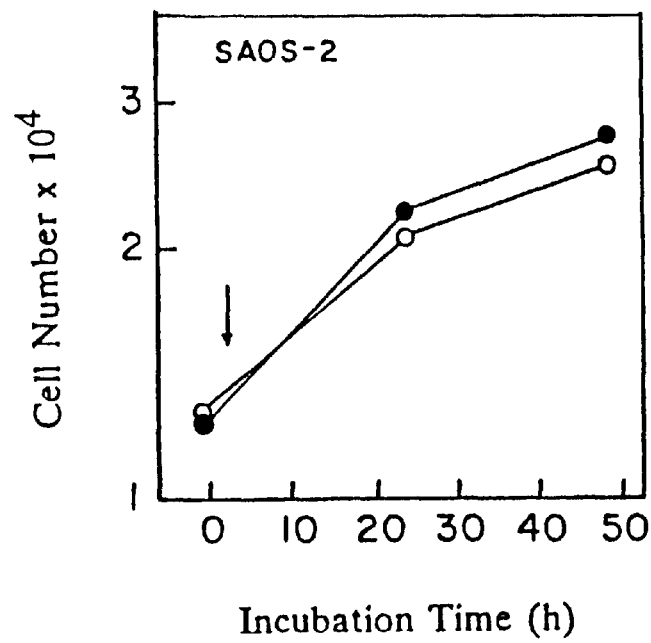
Figure 7A:
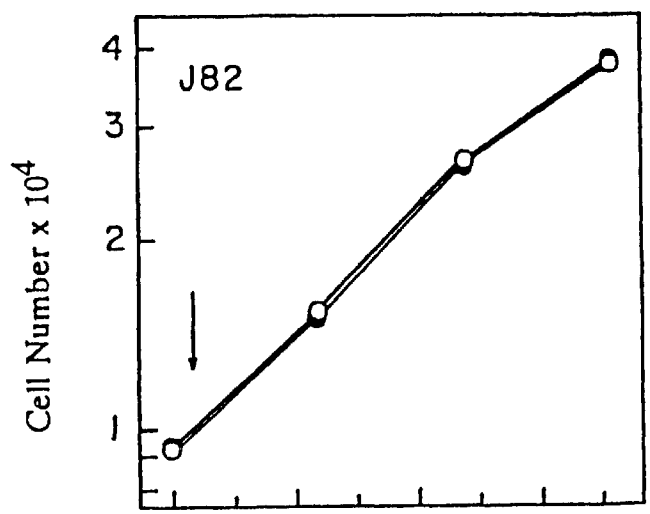
FIG. 7 shows inhibitory factor cell proliferation inhibition assays carried out on the human bladder carcinoma J82
Figure 7B:
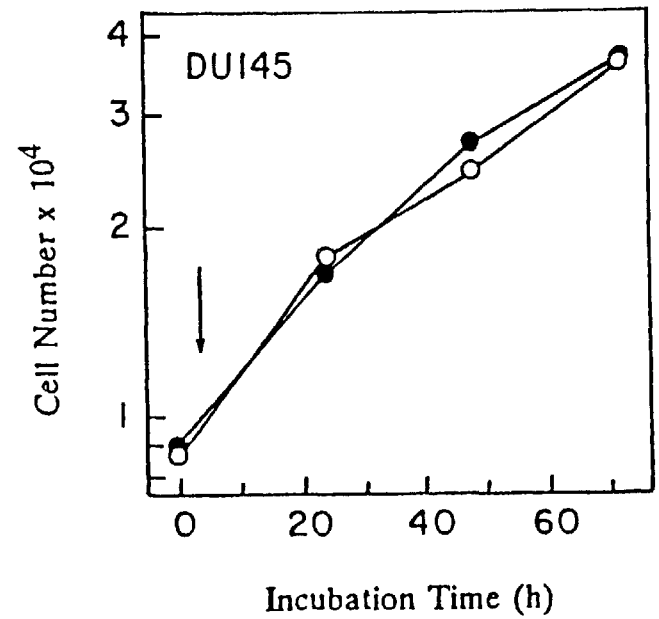

In order to investigate this, the sensitivity of two human osteosarcoma cell lines, U2OS(RB$^+$) and SAOS-2(RB$^-$), to inhibitory factor w ere compared. When $9 \times 10^{-8}$M inhibitory factor was added to the culture medium the U2OS cells were efficiently inhibited within 20 h, while the SAOS-2 cells were refractory to inhibition throughout the incubation period (FIG. 6). Human bladder carcinoma cell line J82 (RB$^-$) and prostate carcinoma cell line DU145 (RB$^-$) also were resistant to the inhibitory action of inhibitory factor (FIG. 7). Even higher concentrations of the inhibitor also were ineffective in blocking cell cycling in RB$^-$ cell lines.

Since cells that express a normal RB product can phenotypically act like RB$^-$ cell lines when transformed with certain DNA tumor antigens, the possibility that these cell lines might also be resistant to the inhibitory influence of inhibitory factor was examined. While normal human keratinocytes were readily arrested by inhibitory factor, the 1321 and NCO papillomavirus E6/E7 protein transformed cell lines were totally refractory to the action of the inhibitor (FIG. 8). The adenovirus E1A protein transformed human epithelial cell line 293 also was resistant to the cell cycle arrest mediated by the inhibitory factor inhibitor (FIG. 9).

Swiss 3T3 cells were found to be sensitive to the inhibitory action of inhibitory factor, while consistent with the observations of papillomavirus and adenovirus transformed human cell lines, the proliferation of both the SV40 large T antigen transformed cell lines SVT2 and F5B were not inhibited by the sialoglycopeptide (FIG. 10). Clearly, the transformation of both human and mouse cells by the transforming antigens of several DNA oncogenic viruses, that are known to sequestered the nuclear RB product, resulted in a refractory phenotype with regard to inhibitory factor action.

Since it has been shown that cells resistant to the inhibitory action of TGF-β can be a reflection of a decrease in the surface receptor population for the ligand, the number of receptors and the $K_d$ of the inhibitor-receptor interaction was measured with the refractory human SAOS-2 and mouse SVT2 cell lines, and compared to the sensitive human U2OS cells. The number of inhibitory factor receptors per cell, and their $K_d$, were remarkably similar.

TABLE 3

Inhibitory Factor Receptors on Sensitive and Insensitive Cell Lines[a]

| Cell Line | Cell Type | Receptors per Cell | $K_d$ (nM) | Inhibitory Factor Mediated Arrest |
|---|---|---|---|---|
| SVT2 | mouse fibroblast | $2.6 \times 10^4$ | 8.5 | Insensitive |
| U2OS | human osteosarcoma | $2.9 \times 10^4$ | 9.7 | Sensitive |
| SAOS-2 | human osteosarcoma | $2.3 \times 10^4$ | 6.1 | Insensitive |

[a]Specific cell receptors for Inhibitory Factor and their $K_d$, were determined with $^{125}$I-radiolabelled inhibitor as described in the Materials and Methods The reason for the refractory nature of RB⁻ and viral transformed cell lines to inhibitory factor cell cycle arrest clearly could not be attributed to a change in cell surface receptors. Consistent with this observation, all cell lines were sensitive to the transient inhibitory factor inhibition of protein synthesis, which requires occupancy of the inhibitory factor receptor to inhibit translational events, whether or not the more enduring cell cycle arrest was effected.

The cell lines used in this study also provided an examination of the potential role of a second tumor suppressor gene product, p53, with regard to the inhibitory action of inhibitory factor. The human carcinoma cell lines J82 and DU145 are p53⁺ while being resistant to the inhibitory action of inhibitory factor.

TABLE 4

Inhibitory Factor Inhibition of Cell Proliferation

| Cell Line | Cell Type | Tumor Suppressor Product (RB) | (p53) | Inhibitory Factor Mediated Inhibition[a] |
|---|---|---|---|---|
| Swiss 3T3 | mouse fibroblast | + | + | + |
| HSBP | human fibroblast | + | + | + |
| HFK | human keratinocte | + | + | + |
| U2OS | human osteosarcoma | + | + | + |
| SAOS-2 | human osteosarcoma | − | − | − |
| DU145 | human prostate carcinoma | − | + | − |
| J82 | human bladder carcinoma | − | + | − |
| 1321 | human keratinocyte | v[b] | v | − |
| NCO | human keratinocyte | v | v | − |
| 293 | human kidney epithelial | v | v | − |
| F5B | mouse fibroblast | v | v | − |
| SVT2 | mouse fibroblast | v | v | − |

[a]The cell lines were examined for sensitivity of cell proliferation with $9 \times 10^{-8}$ M of the Inhibitory Factor inhibitor.
[b]v - Denotes presence of viral oncoproteins capable of sequestering RB and p53.

HL-60 cells, however, are RB⁺ and p53⁻ and are sensitive target cells to the inhibitor. These observations delineate that the RB protein, and not p53 product, appears to play a central role in the ability of inhibitory factor to mediate arrest in the G1 phase of the cell cycle.

Cell cycle arrest of exponentially dividing human and mouse fibroblasts results in cells primarily having the tumor suppressor protein in the $RB^{unphos}$ state (FIG. 4). For all practical purposes it appears that cell cycle arrest, mediated by the cell surface sialoglycopeptide, is equivalent to cells that naturally become arrested by density-dependent growth inhibition (FIG. 5).

Inhibitory factor, derived from a parental cell surface component of bovine cerebral cortex cells, has an unusually broad target cell range. It has the ability to mediate cell cycle arrest of cells obtained from mouse, human, rat, avian and insect species, all of which necessarily have specific cell surface receptors for the inhibitor. In addition, many tumorigenic cell lines, derived by mutation or retroviruses, have been shown to be highly sensitive to the proliferation inhibitor. For the most part, reversal experiments also have shown that this broad array of cells primarily are arrested in the G1 phase of the cell cycle. Studies with mouse and human cells confirm a G1 phase block by the presence of solely the underphosphorylated form of the RB in the inhibited cells. The kinetics of reversal of DNA synthesis, cell doubling and the state of the RB protein are all consistent with the restriction (R) point, near the G1/S interphase. The one exception at the present time to this generality is the inhibitory factor mediated arrest of HL-60 cells. Unlike most others that appear to be synchronously released from cell cycle arrest when the inhibitor is removed, HL-60 cells are irreversibly arrested by the sialoglycopeptide, and even after inhibitory factor is removed the cells progress through differentiation. This is of particular relevance to the present study since the HL-60 cells are p53⁻ and RB⁺. The human osteosarcoma SAOS-2 cell line is p53⁻ and RB⁻ but it appears that the RB protein is the salient gene product with regard to inhibitory factor inhibition of cell cycling. The central role of the RB product in inhibitory factor action was confirmed by the insensitivity of the human bladder J82 (RB⁻ and p53⁺) and human prostate DU145 (RB⁻ and p53⁺) carcinoma cell lines to the inhibitor (FIG. 7).

The insensitivity of RB⁻ mutants and DNA tumor virus transformed cell lines was not associated with neither a reduced level of receptors nor the measured binding affinities of inhibitory factor to U2OS, SAOS-2 and SVT2 cells (Table 3). In fact, the number of inhibitory factor receptors per cell was quite comparable whether or not the cells were growth arrested by the sialoglycopeptide inhibitor, and consistent with earlier measurements of $2 \times 10^4$ receptors per Swiss 3T3 cell that serve as the standard cell line for many of the inhibitory factor studies.

It is clear that the RB product is more than a casual player in the series of metabolic events that mediate cell cycle arrest by the inhibitor. Inhibitory factor arrests cells at a site where the $RB^{unphos}$ state is the dominant form of the tumor suppressor protein. Further, $RB^-$ cell lines are refractory to cell cycle inhibition by a sialoglycopeptide. Either its absence as a functional protein by mutation, or its being sequestered by transforming antigens of certain DNA oncoviruses, led to an insensitivity of cell cycle arrest by the sialoglycopeptide inhibitor (Table 4). The maintenance of the RB product in the hypophosphorylated state alone, although readily seen in growth arrest cells (FIG. 4), is not the sole reason for the refractory nature of these cells. Consistent with the information that the RB protein regulates progression through the cell cycle, there is a requirement for a functional RB protein in order for the cell surface inhibitor to mediate cell cycle arrest.

Inhibitory factor is one of the few naturally occurring potential growth regulators that abrogates the phosphorylation of the RB protein. The inhibitor is a cell surface component that influences cell cycling of a wide variety of cell types. Further, there is a similarity at a molecular level between the inhibitory factor arrested cells and those that naturally reach confluency and quiescence, and the reversibility of its inhibitory action. Inhibitory factor represents a wide class of cell growth regulators that play a fundamental role in density-dependent growth inhibition. In this regard, the inhibitor is a valuable agent for studies of cell cycling, provides a controlled and synchronous population of cells in their progression through the cell cycle, and delineates the genetic and molecular events associated with the posttranslational modifications of the RB product that regulate cell proliferation.

Example IX
The Effect of Inhibitory Factor on Hybridoma Cell Proliferation and Monoclonal Antibody Production Hybridoma cells (3G-10G-5) were plated into 96 well plates at $1 \times 10^4$ cells/well (100 μl medium). Hybridoma line, 3G-10G-5, produces monoclonal antibody to the budgerigar fledgling disease virus (BFDV) major capsid protein (VP1). Inhibitory factor treated (1.2 inhibitory units) experimental cultures (FIG. 11, open circles) had the inhibitor present at the time of plating (FIG. 11, arrow #1). Control cultures received medium without the inhibitor (FIG. 11, closed circles). Fresh medium was not added until seven days of culture. At the times indicated, the cells were pelleted by centrifugation, resuspended and counted, and the media were saved and used to quantitate the monoclonal antibody by ELISA.

On day seven, cells were centrifuged, media were saved, and fresh medium (without inhibitory factor) was added to both control and inhibitor-treated cultures (FIG. 11, arrow #2). On day 11 cells were counted and ELISA carried out. On day 14 cells were counted and tested for viability by Trypan Blue exclusion (FIG. 11, arrow #3).

Trypan Blue exclusion indicated 35%–50% of the cells in the inhibitory factor treated and reversed cultures were viable, while control cultures had ~5% viability.

ELISAs were performed with culture media from days 2, 7 and 11, in 96 well plates containing 90 ng/well of BFDV protein.

The addition of fresh medium is the reason for the second set of lower points for the seventh day.

Hybridoma cells were effectively inhibited by inhibitory factor, and the inhibition is reversible. Antibody synthesis continued while cells were arrested by inhibitory factor and after reversal. [Note that the cell number was almost 30-times greater in control versus inhibitory factor treated cultures.]

TABLE 5

Monoclonal Antibody Production by Hybridoma Cells Incubated with Inhibitory Factor

| Period of Incubation (Days) | | Monoclonal Antibody* | | | |
|---|---|---|---|---|---|
| | | Control | | Inhibitory Factor | |
| | | Total | Per $10^4$ Cells | Total | Per $10^4$ Cells |
| 2 | | 0.10 | 0.09 | 0.05 | 0.07 |
| 7 | (before media change) | 0.33 | 0.02 | 0.18 | 0.45 |
| 7 | (after media change) | 0.05 | — | 0.05 | — |
| 11 | | 1.00 | 0.01 | 0.60 | 1.25 |

Hybridoma cells were incubated for seven days before media were changed and the inhibitory factor removed from the inhibited cultures
*Monoclonal antibody concentrations were measured by Elisa at $(A_{450})$ Example X Cell Cycle Arrest of Yeast Cells

*Saccharomyces cerevisiae*, strain K210-6D, was used in this experiment. Cells were incubated at room temperature where their generation time should approximate 3 hrs. The bovine inhibitory factor used for these studies was purified through TSK-3000 HPLC, and 3 units/250 μl provided complete cell cycle arrest of the standard mouse 3T3 cell line. Each sample was carried out in a single tube and cell numbers were directly determined, by microscopy with a hemocytometer, with individual aliquots that were removed during the incubation.

Inhibition assays were conducted for 6 hrs., with the inhibitor added at 0-time. Reversal experiments were conducted with cultures previously incubated with or without the inhibitor for 6 hrs. at which time the cells were pelleted by centrifugation and resuspended in normal growth medium, and reincubated in the absence of additional inhibitor.

Inhibitory factor readily inhibited proliferation of *S. cerevisiae*, strain K210-6D for at least 6 hrs.

The inhibition caused by 3 units/250 μpl was not evident until 6 hrs. of incubation while inhibition with 15 and 30 units/250 μl was evident within the first 3 hrs. However, reversal of cell cycle arrest did not occur with yeast cells incubated with 15 and 30 units/250 μl, suggesting these higher concentrations may be cytotoxic. In a second experiment the inhibition mediated by 15 units/250 μl of the inhibitory factor was found to be reversible suggesting that this concentration likely borders on the cytotoxic level.

Comparisons of protein synthesis between exponentially growing and inhibitor-arrested yeast cells suggested that at least 60–70% of the arrested cells were viable when 9 or 12 units/250 μl were used. (See Table 6):

TABLE 6

The Effects of Inhibitory Factor on
Protein Synthesis by *Saccharomyces cerevisiae*

| Inhibitor Added (units/250 μl) | CPM | CPM-O-Time* | Protein Synthesis (%) |
|---|---|---|---|
| None (control | 305,758 | 279,706 | 100 |
| 9 | 187,291 | 161,239 | 58 |
| 12 | 227,623 | 201,571 | 72 |
| 15 | 110,192 | 84,140 | 30 |

*O-time 26,052 CPM

Approximately $1 \times 10^6$ cells were incubated in methionine-free medium for 1 hr. The cells were then re-counted and $1 \times 10^6$ cells were added to medium, with and without the inhibitory factor. The cultures were incubated in shaker with 100 μCi/ml of Trans$^{35}$ S-labelled methionine at room temperature for 15 min. The cultures were then diluted with PBS, the cells pelleted by centrifugation, resuspended in alkaline water and the acid-insoluble proteins precipitated with trichloroacetic acid. The proteins were solubilized in 100 μl of water and 50 μl were used to determine protein radioactivity.

However, yeast cells incubated with 15 units/150 μl of the inhibitory factor displayed only 30% protein synthesis in comparison to cultures not treated with the inhibitory factor (Table 6). This again suggested that the higher concentration might inflict cytotoxicity.

Reversal of cell cycle arrest, conducted with yeast cells and 9 or 12 units/150 μl of inhibitory factor showed the inhibition largely to be nontoxic and totally reversible; and, inhibition of yeast cells with 12 units/250 μl of the inhibitory factor was found to be totally reversible and the kinetics of growth after removal of the inhibitory factor showed a 1 hr. lag before the onset of cell division and the culture doubled in the subsequent hour. The recovery indicated that the arrested yeast cells might be synchronized at a specific arrest-site within the cell cycle.

Example XI
Characterization of the Site of Yeast Cell Cycle Arrest

*Saccharomyces cerevisiae,* strain K210-6D was used for this Example. Cells were incubated at room temperature in liquid YDP/U medium (yeast extract, dextrose and peptone medium prepared to contain only 10 μg/ml of uracil). The bovine inhibitory factor used for this Example was purified through TSK-3000 HPLC, and 3 units/250 μl provided complete cell cycle arrest of the standard mouse 3T3 cell line. All studies were carried out with 6 or 9 units/250 μl of the inhibitory factor. Growth inhibition and reversal kinetics were carried out as described in Example X and cell numbers were determined by microscopy with a hemocytometer.

DNA synthesis following growth arrest was measured by incubating cells at room temperature with the inhibitory factor for 4 hrs. The cells were then pelleted by centrifugation and resuspended in 125 μl of YDP/U medium, with or without inhibitory factor, containing 5 μCi of $^3$H-uracil. The cells were reincubated for 2 hrs. at room temperature, pelleted by centrifugation, resuspended in fresh YDP/U medium, and then an equal volume of 2N NaOH was added. The cells were incubated overnight at 37° C., 100 μg/ml of salmon DNA was then added as a carrier, and the DNA was precipitated by the addition of a one-half volume aliquot of ice-cold 50% trichloroacetic acid (TCA). The samples were maintained on ice for 25 min., DNA collected on nitrocellulose filters (0.22 μm pore), and washed three times with cold 5% TCA and once with 95% ethanol. The membranes were then dried and the radiolabelled DNA was measured in a scintillation system.

Yeast cells inhibited with 9 units/250 μl of the inhibitory factor were effectively arrested, and upon removal of the inhibitory factor the cells resumed proliferation and nearly doubled within 2 hrs. of reversal.

Microscopic examination of the growth-arrested yeast cells showed that only a very minor portion of the inhibited cells exhibited visible buds. This was in marked contrast to cells examined from exponentially (uninhibited) growing cultures where a large majority had buds, indicative of rapid cell proliferation. In addition, the growth arrested cells were visibly larger than those examined from the growing cultures. These observations are consistent with what one would expect from *S. cerevisiae* arrested in the G1 phase of the cell cycle.

The kinetics of recovery of the growth-arrested culture, as well as the microscopic appearance of inhibited cells, were consistent with the possibility that the culture was synchronized by incubation with the inhibitory factor.

Two independent experiments illustrated that radiolabelling during the period of reversal of the inhibitory factor-mediated growth arrest led to DNA synthesis prior to cell division (Tables 7 and 8). These observations are consistent with the microscopic studies which suggested that the arrest site was in the G1 phase of the cell cycle.

Most likely, the arrest site of both lower (yeasts) and higher (mammalian) eukaryotic cells are similar, if not identical. This Example confirms and extends the results of Example X regarding the ability of inhibitory factor to inhibit and synchronize *S. cerevisiae* cells in an apparent nontoxic and reversible fashion. The site of the cell cycle where the inhibitory factor mediates its inhibition appears to be similar with both lower and higher eukaryotic cells.

TABLE 7

MEASUREMENT OF DNA SYNTHESIS IN
*S. CEREVISIAE* DURING REVERSAL OF CELL CYCLE
ARREST MEDIATED BY THE SGP (INHIBITORY FACTOR)

Number of cells per culture after 4 hrs
incubation with and without the SGP

| Culture | SGP Inhibitor (units/250 μl) | Cells (125 μl) |
|---|---|---|
| Control | 0 | $1.7 \times 10^5$ |
| Inhibited | 6 | $1.1 \times 10^5$ |

Radiolabelling of SGP-inhibited and reversed cultures
(2 hrs of reincubation)

| Culture | SGP Inhibitor During Re-incubation | Total Cells (125 μl) | Total $^3$H-Uracil Incorporated (CPM) | Minus 0-Time Background Control[1] (CPM) | Normalized for Cell Number[2] (CPM) |
|---|---|---|---|---|---|
| Control | NO | $3.2 \times 10^5$ | 20,772 | 14,296 | 10,211 |
| Inhibited | Yes | $1.5 \times 10^5$ | 5,327 | <100 | <100 |
| Control | NO | $3.3 \times 10^5$ | 36,016 | 29,540 | 21,100 |
| Inhibited | NO | $3.0 \times 10^5$ | 17,440 | 10,964 | 10,964 |

[1]0-time controls, to obtain nonspecific precipitated radioactivity, were determined by terminating the incubation immediately after the addition of the $^3$H-uracil. The average for three independent samples was 6,476 CPM.
[2]Normalized for the relative number of cells after 4 hrs of incubation that would have doubled during the 2 hrs of reincubation.

TABLE 8

MEASUREMENT OF DNA SYNTHESIS IN
*S. CEREVISIAE* DURING REVERSAL OF CELL CYCLE
ARRESTED MEDIATED BY THE SGP (INHIBITORY FACTOR)

Number of cells per culture after 4 hrs
incubation with and without the SGP

| Culture | SGP Inhibitor (units/250 µl) | Total Cells (100 µl) |
| --- | --- | --- |
| Control | 0 | $5 \times 10^5$ |
| Inhibited | 6 | $3 \times 10^5$ |
| Inhibited | 9 | $3 \times 10^5$ |

Radiolabelling of SGP-inhibited and reversed cultures
(2 hrs of reincubation incubation)

| Culture | SGP Inhibitor During Reincubation | Total Cells (100 µl) | Total $^3$H-Uracil Incorporated (CPM) | Minus 0-Time Background Control[1] (CPM) | Normalized for Cell Number[2] (CPM) |
| --- | --- | --- | --- | --- | --- |
| Control | NO | $9.0 \times 10^5$ | 50,234 | 40,124 | 23,602 |
| Inhibited (6) | Yes (6) | $3.1 \times 10^5$ | 12,615 | 2,505 | 2,505 |
| Inhibited (9) | Yes (9) | $3.3 \times 10^5$ | 13,775 | 3,665 | 3,665 |
| Control | NO | $8.4 \times 10^5$ | 35,472 | 25,362 | 15,272 |
| Inhibited (6) | NO | $7.3 \times 10^5$ | 33,319 | 23,209 | 23,209 |
| Inhibited (9) | NO | $7.0 \times 10^5$ | 35,401 | 25,291 | 25,291 |

[1]0-time controls, to obtain nonspecific precipiated radioactivity, were determined by terminating the incubation immediately after the addition of the $^3$H-uracil. The average for three independent samples was 10,110 CPM.
[2]Normalized for the relative number of cells after 4 hrs of incubation that would have doubled during the 2 hrs of reincubation.

Example XII

Effects of Inhibitory Factor on Neoplastic Cell Lines Derived from the Nervous System Nerve Growth Factor (NGF) has long been used as a model system for the differentiation of cells of neuronal origin, particularly rat PC-12 (pheochromocytoma) cells. Although NGF induces morphological changes in PC-12 cells, NGF does not cause the same morphological changes in mouse N2a (neuroblastoma) cells but rather it acts as a mitogen in these cells. Treatment of PC-12 and N2a cells with inhibitory factor resulted in the induction of neurite extension in both cell lines. Both cell lines responded in a similar manner to inhibitory factor treatment, with at least 50–60% of the cells producing neurite outgrowth within three days of exposure to inhibitory factor. Within 5–6 days 80–90% of the inhibitory factor treated cells exhibited extensive neurite outgrowth. However, the PC-12 cells were three times more sensitive to inhibitory factor induced neurite extension as compared to the N2a cells.

N2a cells, like many other nontransformed and transformed cells, were sensitive to the growth inhibitory influence of bovine inhibitory factor. Within 24 hours of the addition of $6 \times 10^{-8}$M inhibitory factor cell proliferation was remarkedly reduced, and without the addition of fresh inhibitor during the incubation period, cell division resumed in approximately 48 hours. A concentration of $4 \times 10^{-8}$M of the inhibitory factor was less inhibitory and a reduction in N2a cell number was only seen after 48 hours of incubation.

PC-12 cells also were sensitive to growth arrest by inhibitory factor, and proved to be approximately three- to six-times more sensitive that the N2a cell line. Growth inhibition was readily observed within 48 hours when the cells were incubated with either $1 \times 10^{-8}$M or $1.5 \times 10^{-8}$M inhibitory factor. Cell cycle arrest with these concentrations persisted for at least 72 hours. A concentration of $2 \times 8^{-8}$M inhibitory factor appeared to be cytotoxic to these cells since the cell number decreased during the first 48 hours of incubation.

Unlike the inhibitory factor, NGF was capable of eliciting a morphological differentiation response only with the PC-12 cells, and the N2a neuroblastoma cell line did not respond in a similar manner. The morphological differentiation induced by inhibitory factor with both PC-12 and N2a cells was readily reversible. Upon removal of inhibitory factor, the extended neurites began to retract within a matter of hours and within a few days the cells resumed their blast-like morphology. Concomitant to the alteration in cell morphology when the inhibitory factor was removed, cell cycle arrest was reversed and the cells again began to proliferate. The reversibility of the inhibitory factor-induced cell cycle arrest with PC-12 and N2a cells was in marked contrast to the irreversible nature of the inhibition previously observed with human HL-60 cells.

The transformed PC-12 and N2a cell lines were readily growth inhibited by the inhibitory factor. Unlike HL-60 cells, however, these neuronally-derived cell lines resumed cell division upon the removal of the inhibitory factor. PC-12 cells were at three- to six-times more sensitive to the growth inhibitory activity of the inhibitory factor when compared to N2a cells. Along with the cell cycle arrest mediated by the inhibitory factor, both PC-12 and N2a cells underwent extensive morphological differentiation. The differentiation was visibly manifested by a progressive extension of neurites from the perikaryon. Within the limits of these experiments, the neurites remained extended, and cell cycle arrest endured as long as the inhibitory factor was present in the incubation medium. Upon removal of the inhibitory factor, by medium replacement, the neurites were retracted. In addition to the reversibility of the morphological differentiation features, a concomitant reentry of the cells to cell cycling ensued.

When the biological properties of nerve growth factor (NGF) and the inhibitory factor were compared, some important differences were observed. NGF did induce morphological differentiation with PC-12 cells, but did not elicit a similar differentiation response with N2a cells. NGF also did not mitotically arrest N2a cells as was observed with the inhibitory factor.

Example XIII

Role of Intracellular Calcium Regulation in Growth in the Section Induced by Inhibitory Factor Studies were carried out to investigate the potential importance of intracellular calcium regulation in the mechanism of action of the inhibitory factor. Three mouse keratinocyte cell lines showed increased sensitivity to the growth inhibitory effects of the inhibitory factor (60-fold), and the sensitivity of these cell lines, as well as Swiss 3T3 cells, could be altered by changing the extracellular calcium concentration. Lowering extracellular calcium concentrations increased sensitivity and increasing extracellular calcium concentrations decreased sensitivity to the growth inhibitory effects of the inhibitory factor. Exposure to A23187 or thapsigargin simultaneously with, or prior to, the addition of the inhibitory factor had no effect on growth inhibition.

Sensitivity of Mouse Keratinocyte Cell Lines to the Growth Inhibitory Action of the Inhibitory Factor Immortalized C50 mouse keratinocytes, transformed 308 mouse keratinocytes, and PDVC57 neoplastic mouse keratinocytes were treated at time 0 with: PBS; $3\times10^{-10}$ M inhibitory factor; or, $5\times10^{-10}$M inhibitory factor. Cell proliferation was monitored in 48-well plates each day for three days.

Effect of the Extracellular Calcium Concentration on Inhibitory Factor-Induced Growth Inhibition in 308 Transformed Mouse Keratinocytes Cells were treated at time 0 with PBS (see FIG. 12 open squares), $5\times10^{-10}$M inhibitory factor (filled boxes), $5\times10^{-9}$M inhibitory factor (open circles), or $3\times10^{-8}$M inhibitory factor (filled circles) in Eagles's minimal essential medium containing (A) 0.05 mM $Ca^{2+}$ or (B) 1.4 mM $Ca^{2+}$. Cell proliferation was monitored in 48-well plates at the times indicated at FIG. 12.

Effect of the Extracellular Calcium Concentration on Inhibitory Factor-Induced Growth Inhibition of S3T3 Mouse Fibroblasts Cells were treated at time—with PBS (see FIG. 13 open squares), $5\times10^{-10}$M inhibitory factor (filled boxes), $5\times10^{-9}$M inhibitory factor (open circles), or $3\times10^{-8}$M inhibitory factor (filled circles)in Eagle's minimal essential medium containing (A) 1.8 mM $Ca^{2+}$ or (B) 0.18 mM $Ca^{2+}$. Cell proliferation was monitored in 48-well plates at the times indicated in FIG. 13.

Effect of the Calcium Ionophore A23187 or Thapsigargain on Inhibitory Factor-Induced Growth Inhibition of S3T3 Mouse Fibroblasts A) S3T3 cells, grown in 48-well plates, were treated at time 0 with PBS, 2 μg/ml of A23187, or plus inhibitory factor.

B) All S3T3 cell cultures were grown as monolayers in 48-well plates. Two sets of cultures were incubated with either PBS or 250 nM thapsigargin for the entire 72 hr. incubation period. Another set of cultures were treated with 250 nM thapsigargin for 15 hrs. and then 250 nM thapsigargin plus $3\times10^{-8}$ inhibitory factor were added. Other sets of cultures were treated at time 0 with PBS, and 15 hrs. later were again treated with $3\times10^{-8}$ inhibitory factor, 250 mM thapsigargin, or thapsigargin with inhibitory factor.

The three mouse keratinocyte cell lines (immortalized, transformed, and neoplastic) exhibited increased sensitivity (60- to 100-fold) to inhibitory factor-induced growth inhibition as compared to other cell types previously tested. No correlation between the degree of sensitivity and the degree of transformation was observed. Sensitivity to inhibitory factor-induced growth inhibition could be altered by simply altering the extracellular calcium concentration of both mouse keratinocytes (308 cells) and Swiss 3T3 (S3T3) fibroblasts, with cells exhibiting an inverse correlation between extracellular calcium concentration and sensitivity to inhibitory factor-induced growth inhibition. Altering the extracellular $Ca^{2+}$ concentration does appear to increase the intracellular $Ca^{2+}$ concentration in the 208 mouse keratinocyte cell line and the S3T3 mouse fibroblast line, as measured by cell associated $^{45}Ca^{2+}$.

Exposure of S3T3 mouse fibroblasts to the calcium ionophore A23187 (2 μg/ml) or thapsigargin (250 nM) prior to, or simultaneously with, the inhibitory factor did not affect inhibitory factor-induced growth inhibition, although A23187 could block the transient inhibitory factor-induced protein synthesis inhibition.

Exposure of neoplastic mouse keratinocytes 9PDVC57) cells) to the inhibitory factor produced no characteristic change in the serum-induced increase in $^{45}Ca^{2+}$ influx and efflux. The inhibitory factor could, however, inhibit the release of $Ca^{2+}$ from intracellular stores induced by TPA in S3T3 fibroblasts.

Calcium regulation plays an important role in the mechanism of action of the inhibitory factor in growth inhibition, and the point of regulation may involve altering intracellular $Ca^{2+}$ storage and/or release. By altering calcium levels, the sensitivity of the assays of the subject invention can be increased.

While the present invention has been described in terms of preferred embodiments, it is understood that variations and modifications will occur to those skilled in the art. Therefore, it is intended that the appended claims cover all such equivalent variations which come within the scope of the invention as claimed.

The features disclosed in the foregoing description, in the following claims and/or in the accompanying drawings may, both separately and in any combination thereof, be material for realizing the invention in diverse forms thereof.

What is claimed is:

1. A purified inhibitory peptide, free of protease activity, having a molecular weight of approximately 18 kD as determined SDS PAGE, wherein said peptide inhibits cell division or cell cycling.

2. A purified inhibitory peptide as in claim 1, wherein said peptide reversibly arrests cell cycling in cells from mouse, monkey or human tissue.

3. A purified inhibitory peptide as in claim 1, wherein said peptide is a sialoglycopeptide.

4. A purified inhibitory peptide as in claim 1, wherein said peptide arrests cell cycling in the G1 phase.

5. A purified inhibitory peptide as in claim 1, wherein said peptide arrests cell cycling in fibroblast and epithelial cells.

6. A purified inhibitory peptide as in claim 1, wherein said peptide is a bovine or human peptide.

7. The purified inhibitory peptide of claim 1, wherein said peptide has a detectable label.

8. A composition comprising the purified inhibitory peptide of claim 1 and a pharmaceutically acceptable carrier.

9. A purified inhibitory membrane-associated peptide having a molecular weight of approximately 66 kD as determined by SDS PAGE, wherein said peptide inhibits cell division or cell cycling.

10. A purified inhibitory peptide as in claim 9, wherein said peptide reversibly arrests cell cycling in cells from mouse, monkey or human tissue.

11. A purified inhibitory peptide as in claim 9, wherein said peptide is a sialoglycopeptide.

12. A purified inhibitory peptide as in claim 9, wherein said peptide arrests cell cycling in the G1 phase.

13. A purified inhibitory peptide as in claim 9, wherein said peptide arrests cell cycling in fibroblast and epithelial cells.

14. A purified inhibitory peptide as in claim 9, wherein said peptide is a bovine or human peptide.

15. The purified inhibitory peptide of claim 9, wherein said peptide has a detectable label.

16. A composition comprising the purified inhibitory peptide of claim 9, and a pharmaceutically acceptable carrier.

* * * * *